United States Patent [19]
Taylor et al.

[11] Patent Number: 5,882,198
[45] Date of Patent: Mar. 16, 1999

[54] ENDODONTIC INSTRUMENT HAVING ENHANCED COMPLIANCE AT THE TIP

[75] Inventors: Tim L. Taylor, Corona Del Mar, Calif.; John T. McSpadden, Chattanoga, Tenn.

[73] Assignee: Ormco Corporation, Orange, Calif.

[21] Appl. No.: 885,390

[22] Filed: Jun. 30, 1997

[51] Int. Cl.⁶ .................................................. A61C 5/02
[52] U.S. Cl. .................................................. 433/102
[58] Field of Search .................................................. 433/102

[56] References Cited

U.S. PATENT DOCUMENTS

| | | |
|---|---|---|
| 1,022,838 | 4/1912 | Funk . |
| 1,067,015 | 7/1913 | Fowler . |
| 1,211,537 | 1/1917 | Burton . |
| 1,307,446 | 6/1919 | Kerr . |
| 2,035,298 | 3/1936 | Caldwell . |
| 2,084,737 | 6/1937 | Magnus . |
| 2,328,629 | 7/1943 | Eich et al. . |
| 2,769,355 | 11/1956 | Crisp . |
| 2,966,081 | 12/1960 | Kallio . |
| 3,443,459 | 5/1969 | Mackey et al. . |
| 3,947,143 | 3/1976 | Gulla ................................ 408/230 |
| 3,971,135 | 7/1976 | Leu .................................. 433/165 |
| 3,991,454 | 11/1976 | Wale ................................ 29/105 R |
| 4,190,386 | 2/1980 | Brabetz et al. ..................... 408/1 R |
| 4,209,275 | 6/1980 | Kim .................................. 408/211 |
| 4,330,229 | 5/1982 | Croydon .............................. 408/212 |
| 4,332,561 | 6/1982 | McSpadden .......................... 433/102 |
| 4,457,710 | 7/1984 | McSpadden ........................... 433/81 |
| 4,536,159 | 8/1985 | Roane ................................. 433/224 |
| 4,538,989 | 9/1985 | Apairo et al. ...................... 433/102 |
| 4,602,900 | 7/1986 | Arpaio et al. ...................... 433/102 |
| 4,661,061 | 4/1987 | Martin .............................. 433/102 |
| 4,758,156 | 7/1988 | Johnson ............................. 433/81 |
| 4,836,780 | 6/1989 | Buchanan ........................... 433/102 |
| 4,871,312 | 10/1989 | Heath ............................... 433/164 |
| 4,894,011 | 1/1990 | Johnson ............................. 433/81 |
| 4,904,185 | 2/1990 | McSpadden .......................... 433/164 |
| 4,913,603 | 4/1990 | Friedli et al. ..................... 408/230 |
| 4,934,934 | 6/1990 | Arpaio et al. ...................... 408/230 |
| 4,971,556 | 11/1990 | Ritano .............................. 433/102 |
| 5,017,138 | 5/1991 | Schilder ............................ 433/102 |
| 5,026,284 | 6/1991 | Martin .............................. 433/102 |
| 5,035,617 | 7/1991 | McSpadden .......................... 433/102 |
| 5,035,618 | 7/1991 | Katz et al. ........................ 433/102 |
| 5,088,863 | 2/1992 | Imanaga et al. ..................... 408/230 |
| 5,104,316 | 4/1992 | McSpadden .......................... 433/102 |
| 5,106,298 | 4/1992 | Heath et al. ....................... 433/102 |
| 5,125,838 | 6/1992 | Seigneurin .......................... 433/102 |
| 5,219,284 | 6/1993 | Velvart et al. ..................... 433/102 |
| 5,257,934 | 11/1993 | Cossellu ............................ 433/102 |
| 5,380,200 | 1/1995 | Heath et al. ....................... 433/102 |
| 5,387,059 | 2/1995 | Borzemsky .......................... 408/226 |
| 5,464,362 | 11/1995 | Heath et al. ....................... 451/48 |
| 5,503,554 | 4/1996 | Schoeffel .......................... 433/102 |

FOREIGN PATENT DOCUMENTS

| | | |
|---|---|---|
| 0195838 | 12/1989 | European Pat. Off. . |
| 775073 | 6/1934 | France . |
| 279144 | 10/1913 | Germany ............................ 430/102 |
| 949002 | 3/1956 | Germany . |
| 622588 | 5/1978 | U.S.S.R. . |
| 715238 | 2/1980 | U.S.S.R. . |
| 1419624 | 12/1975 | United Kingdom .................... 408/230 |
| 2035806 | 12/1977 | United Kingdom . |

*Primary Examiner*—Cary E. O'Connor
*Attorney, Agent, or Firm*—Wood, Herron & Evans

[57] ABSTRACT

An endodontic instrument is provided for use in performing root canal procedures and comprises an elongate working portion and a chisel tip portion which has removing edges that improve the effectiveness of the instrument in extirpating and enlarging the root canal. The working portion has a non-uniform taper which accelerates from a proximal end of the instrument to a distal end forming a region of enhanced compliance adjacent the tip.

13 Claims, 8 Drawing Sheets

ENDODONTIC INSTRUMENT HAVING ENHANCED COMPLIANCE AT THE TIP

BACKGROUND

1. Field of the Invention

This invention relates generally to the field of endodontic instruments and more particularly to reamers or files used in performing root canal procedures. These instruments are used to remove diseased tissue from the canal prior to sealing and filling the canal cavity with a suitable filler material, such as gutta-percha.

2. Description of the Related Art

One of the more technically difficult and delicate procedures in the field of dentistry is root canal therapy. The root canal of a tooth houses the circulatory and neural systems of the tooth. These enter the tooth at the terminus of each of its roots and extend through a narrow, tapered canal system to a pulp chamber adjacent the crown portion of the tooth. If this pulp tissue becomes diseased or injured, it can cause severe pain and trauma to the tooth, sometimes necessitating extraction of the tooth. Root canal therapy involves removing the diseased tissue from the canal and sealing the canal system in its entirety. If successful, root canal therapy can effectively alleviate the pain and trauma associated with the tooth so that it need not be extracted.

To perform a root canal procedure, the endodontist first drills into the tooth to locate the root canal and then uses instruments of small diameter such as reamers and files to remove the decayed, injured or dead tissue from the canal. These are typically elongated instruments which are rotated and/or reciprocated within the root canal. The primary goal is to remove all of the decayed or injured nerve while leaving the integrity of the root canal walls relatively unaffected. Preserving the integrity of the root canal is important in order to allow proper filling of the root canal void in a homogenous three dimensional manner such that leakage or communication between the root canal system and the surrounding and supporting tissues of the tooth is prevented. Once as much of the diseased material as practicable is removed from the root canal, the canal is then sealed closed, typically by reciprocating and/or rotating a condenser instrument in the canal to urge sealing material such as gutta-percha into the canal.

Root canals are not necessarily straight and are often curved or convoluted. Therefore, it is often difficult to clean the canal while preserving its natural shape. Many instruments have a tendency to straighten out the canal or to proceed straight into the root canal wall, altering the natural shape of the canal and sometimes transporting completely through the canal wall. Also, the openings of many root canals are small, particularly in older patients, due to calcified deposits on the root canal inner walls. Thus the files or reamers must be able to withstand the torsional load necessary to penetrate and enlarge the canal opening without breaking the instrument.

To preserve the natural shape of the root canal and to facilitate insertion of the tip of the instrument into small root canal openings, traditional reamers or files have an elongated working portion having a uniform taper such that the diameter of the working portion increases uniformly from a small diameter at the tip of the instrument to a larger diameter at the base of the working portion. The taper rate may vary from instrument to instrument and commonly ranges from about 0.02 mm/mm to about 0.08 mm/mm. Helical flutes defining cutting edges are typically provided along the tapered working portion to promote tissue removal and desired shaping of the root canal and advancement of dental chips and debris up the expanding diameter of the instrument along the helical flutes and away from the tip of the instrument.

One problem with traditional endodontic instruments used for extirpating and filling a root canal is that the torsional limitations of the instrument are often exceeded, resulting in breakage of the instrument in the canal. Breakage of the instrument can occur as a result of inadequate removal of dental chips which are cut from the wall of the root canal. These dental chips often become engaged between the instrument and the root canal wall resulting in increased friction and excessive torque on the instrument. Inadequate chip removal may occur particularly at or near the tip of the instrument where the flutes are relatively shallow. Build up of debris between the flutes and the canal wall can cause damage to the canal walls and/or inadequate or uneven tissue removal and can also lead to failure of the instrument.

Another problem that can occur is transportation or penetration through the canal wall. This can occur when a straight file or reamer is used to prepare a curved canal. The file often will tend to maintain a straight path into the root canal wall instead of following the natural path of the canal. In some extreme cases, the file can actually perforate or penetrate the wall of the root canal causing injury to the supporting tissues of the tooth. One prior attempt to solve this problem was to provide a dental file or reamer having a smooth-walled, non-cutting pilot tip for guiding the file or reamer into the curved root canal. See, for instance, U.S. Pat. No. 4,299,571 to McSpadden, incorporated herein by reference. While the provision of such a smooth-walled pilot tip represented a significant improvement in the art at the time, the design has several significant drawbacks in certain cases.

One drawback is that the pilot tip, being blunt and smooth, has little or no cutting ability. While the blunt tip can fairly easily wedge its way into the soft, fleshy nerve, there is often difficulty encountered in a calcified root canal which has layers of calcified accretion built up along the inner wall of the canal. It is often difficult in these highly calcified root canals to penetrate through the calcified material to a depth sufficient to allow cutting to begin. When using such files having a blunt tip, the file must essentially burnish or grind its way into the calcified material before entering the canal. This generates significant heat and friction as the tip attempts to burnish its way through the hard calcified material. This can cause pain and heating of the tooth which is undesirable. It can also cause increased torsional loads on the file or reamer which can increase the risk of breakage in the canal and decrease the life of the tool.

SUMMARY OF THE INVENTION

The present invention is directed to an improved endodontic instrument design for use in an endodontic root canal procedure. The instrument generally comprises an elongated working portion having a length of from about 3 to about 18 millimeters, a peripheral diameter ranging from about 0.08 millimeters to about 1.9 millimeters, at least one helical flute, at least one helical land and at least one tissue-removing edge. Each flute and land has a pitch ranging from about 1 spiral per 16 millimeters to about 1 spiral per millimeter.

In accordance with one preferred embodiment, the above-described working portion has a chisel tip adjacent the distal end of the working portion. The chisel tip comprises plural facets which intersect along a substantially linear chisel edge that is substantially orthogonal to a longitudinal axis of the elongate working portion. The facets integrate with the flutes to define additional tissue-removing edges at the tip of the instrument. When rotated in a root canal the chisel edge loosens decayed or diseased tissue and the tissue-removing edges at the tip of the instrument cuts the tissue and as the file progresses down the root canal. In another preferred embodiment, the chisel tip has asymmetric proportions such that the tip will tend to wobble or wonder as it progresses down the root canal.

In accordance with another preferred embodiment the invention comprises an endodontic dental instrument for extirpating and enlarging a root canal, comprising a working portion in which at least a portion of the working portion is tapered either in diameter, web thickness, or both, and terminates at a tip. The rate of taper adjacent the tip is greater than the rate of taper in the remainder of the working portion.

In accordance with another preferred embodiment the invention comprises an endodontic dental instrument for extirpating and enlarging a root canal, comprising a working portion having a proximal end portion and a distal end portion and terminating at a tip. The distal end portion further includes a region of locally enhanced compliance adjacent the tip. The enhanced compliance adjacent the tip allows the instrument to more readily follow the central axis of a curved root canal with less tendency to transport through the canal wall. The region of locally enhanced compliance can be achieved in any number of ways such as by accelerating the rate of web taper and/or diameter taper in that region and/or by annealing or treating the region chemically or thermally so as to produce enhanced compliance characteristics. Additional flutes, recesses and/or other features can also be provided to provide locally enhanced compliance in a desired region of the working portion of the instrument.

In accordance with another preferred embodiment the invention comprises an endodontic dental instrument for extirpating and enlarging a root canal, comprising a working portion having a proximal end portion and a distal end portion and terminating at a tip. The working portion is divided into at least two regions, including a first region extending from a first point adjacent the proximal end portion to a second point intermediate the proximal and distal end portions and a second region adjacent the first region and extending from the second point to a third point adjacent the distal end portion of the working portion. The working portion has a stiffness in the first region which decreases substantially continuously along a first curve progressively from the first point to the second point. The stiffness of the working portion in the second region decreases substantially continuously along a second curve, steeper than the first curve, progressively from the second point to the third point.

These and other features and embodiments of the present invention will become readily apparent to those skilled in the art, having reference to the following detailed description and accompanying drawings, the invention not being limited, however, to any particular preferred embodiment disclosed or shown.

BRIEF DESCRIPTION OF THE DRAWINGS

The figures shown and described below illustrate particular preferred embodiments of endodontic instruments having various working portion and tip configurations. The particular instruments shown are illustrated as reamers or files. However, it should be understood that these instruments can also be configured for use as condensers or compactors by reversing the direction of twist of the helical flutes and lands and/or reversing the direction of rotation of the instrument as will be readily apparent from the detailed description having reference to the appended figures, of which.

DETAILED DESCRIPTION OF THE PREFERRED EMBODIMENTS

Figure 1:
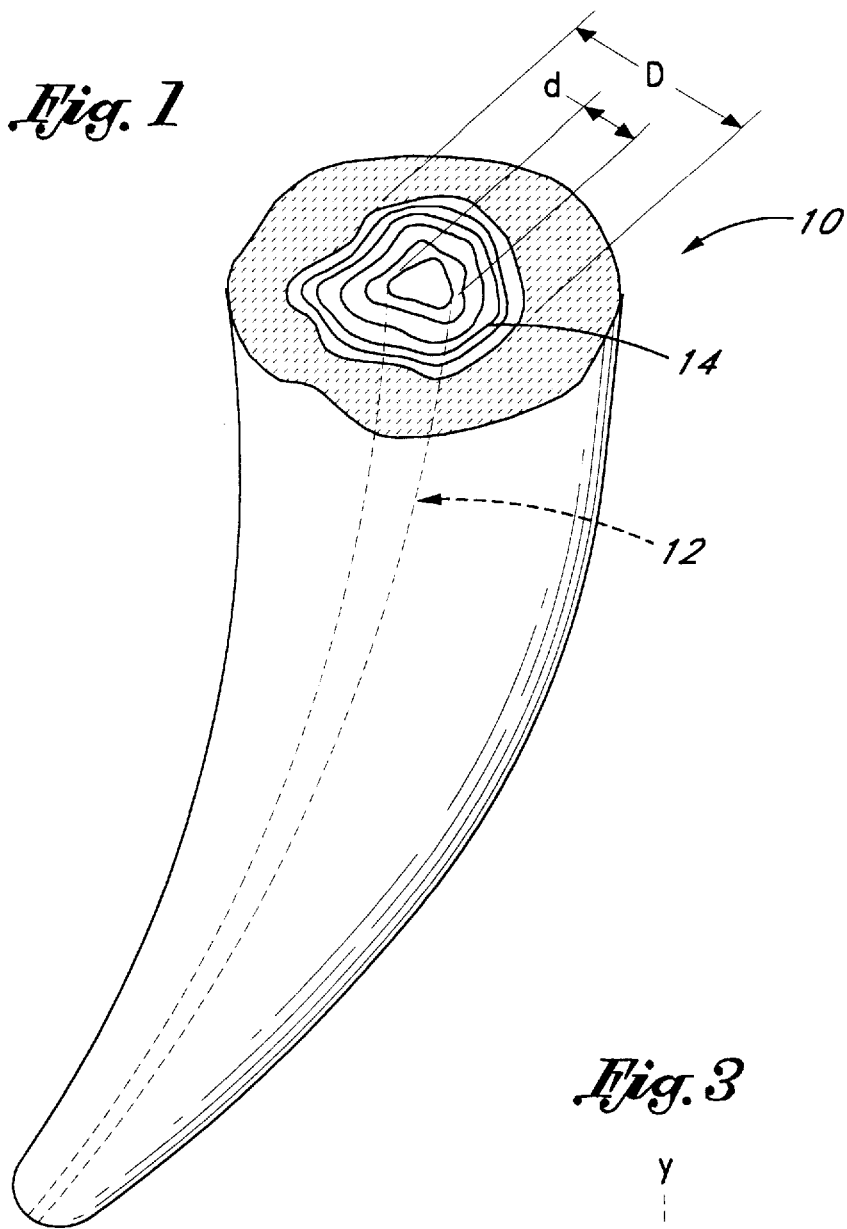
FIG. 1 is a representational partial schematic drawing of a typical calcified root canal.
Figure 3:
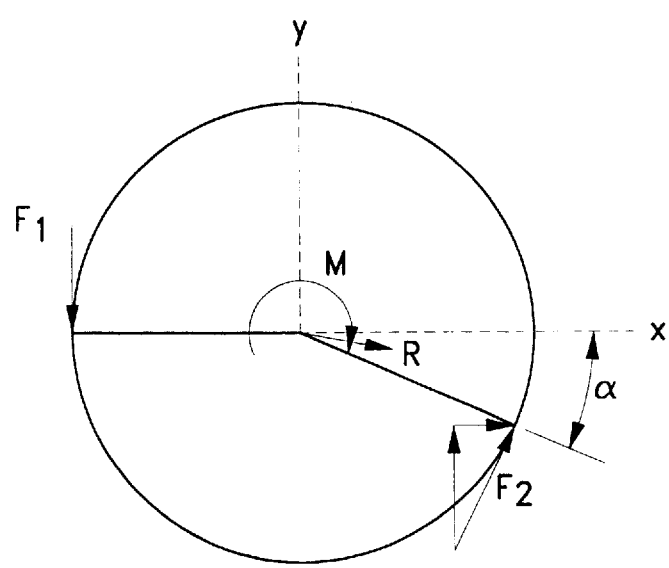
FIG. 3 is a schematic free body diagram illustrating the effects of asymmetric forces exerted on the chisel tip of an endodontic instrument having features as disclosed herein.

As noted above, a significant drawback of conventional endodontic files or reamers is that the tip is typically blunt or smooth and, therefore, has little or no cutting ability. While a blunt tip can easily wedge its way into the soft, fleshy nerve, there is often difficulty encountered in root canals, particularly in older patients, which have become built up with layers of calcified accretion along the inner wall of the canal. This is illustrated in FIG. 1. The opening of the root canal 12 would normally be of diameter "D." But as shown in FIG. 1 the opening of a calcified root canal may be reduced to a much smaller diameter "d." Again, this is due to the build up of layers of calcified accretion 14 within the root canal 12 of the root structure 10.

For these small root canal openings it is difficult to enter the canal with a conventional file having a blunt or rounded tip because the tip of the instrument has little or no cutting or abrading ability. Rather, the instrument must grind or burnish its way into the canal before any cutting action takes place. Even then, the cutting action only occurs at the periphery of the instrument and not at the tip of the instrument which continues to grind or burnish its way down the canal. This increases the wear and tear on the instrument, increases the risk of breakage and, in addition, can cause heating in the canal and resulting damage to surrounding tissues. Also, the root canal procedure takes longer to complete, resulting in increased cost and discomfort to the patient.

One possible solution would be to make the tip of the instrument smaller than the reduced diameter "d" of the calcified canal 12. But there is a practical limit to how small the tip can be made on a conventional uniformly tapered endodontic file without compromising the integrity of the instrument. Conventional tapered files have tip diameters that are as small as 0.06 mm corresponding to a size "06" file. But even these small instruments have difficulty penetrating into root canal openings having significant calcium build up. Moreover, making such conventional instruments any smaller could lead to failure of the instrument in the canal.

The present invention solves these and other problems by providing, in one embodiment, a tip having improved cutting ability. It was heretofore widely believed that the use of a cutting tip would lead to an increased likelihood of canal wall transportation. To the contrary, the present invention, in one embodiment, involves the discovery that providing at least some cutting ability on the tip can increase the overall cutting efficiency and clinical efficacy of the instrument without significantly increasing the likelihood of canal wall transportation. As will be explained in more detail below, the particular file configurations and tip geometries disclosed and described herein reduce the cutting friction between the instrument and the tooth canal, improve cutting efficiency and performance of the instrument, while reducing the tendency of the instrument to fail under torsional stress.

Figure 2A:
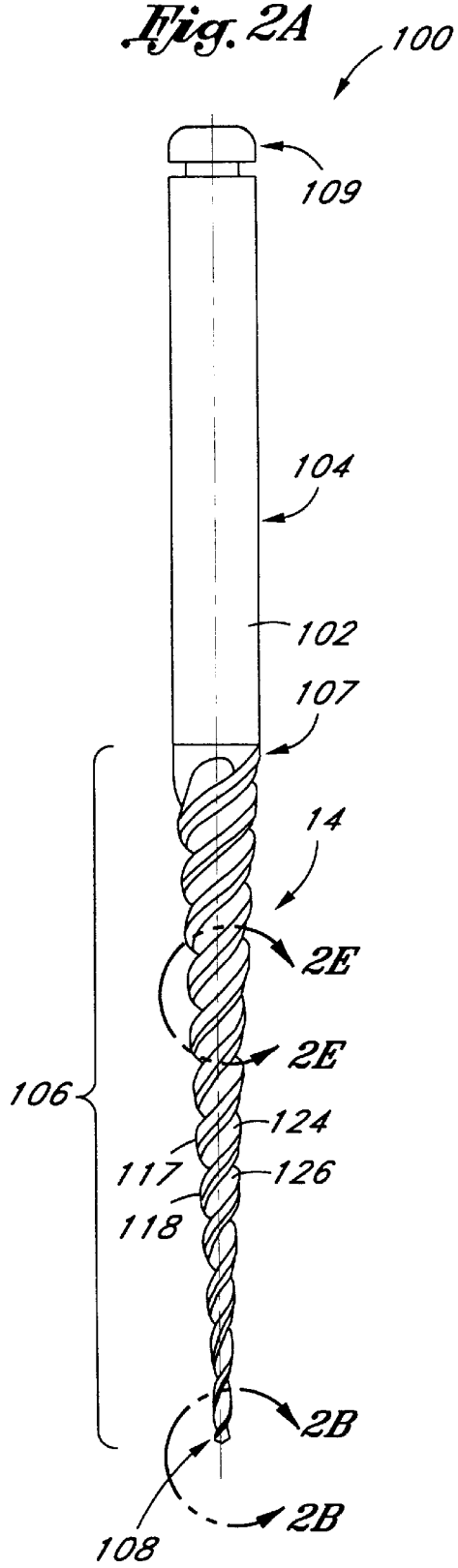
FIG. 2A is an elevational view of a reamer instrument including a chisel tip.
Figure 2E:
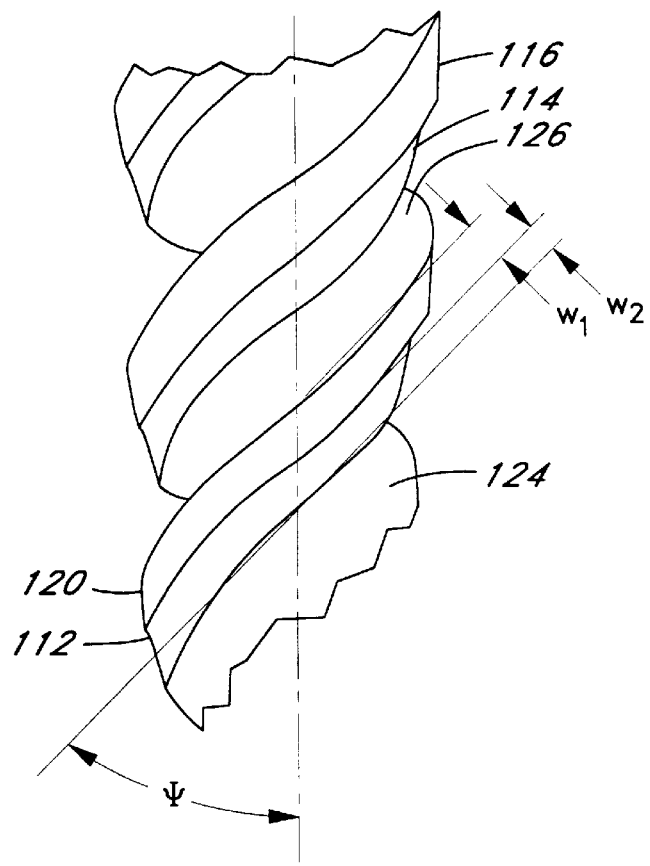
FIG. 2E is a detail side elevational view of the working portion of the reamer instrument shown in FIG. 2A.
Figure 2B:
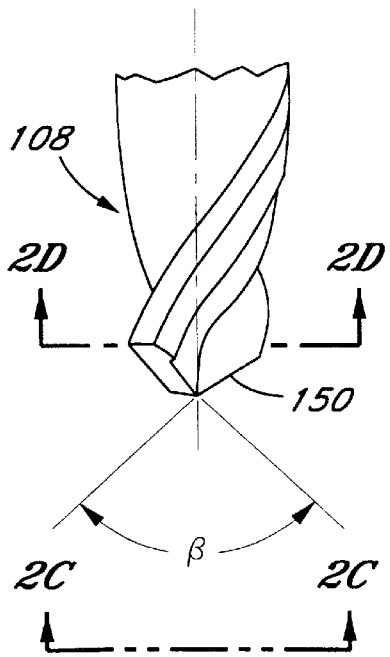
FIG. 2B is a detailed side elevational view of the distal end portion of the endodontic reamer of FIG. 2A.
Figure 2C:
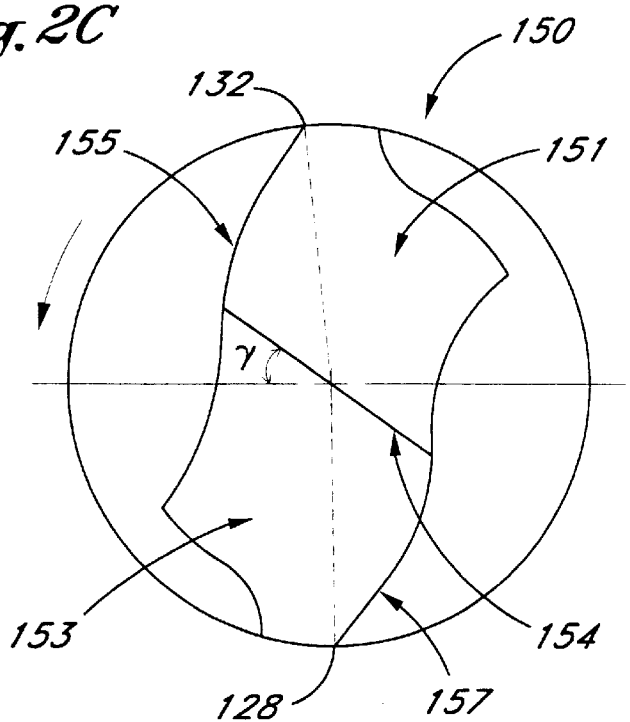
FIG. 2C is a detail end view of the chisel tip of the reamer of FIG. 2A.

FIGS. 2A–E illustrate one preferred embodiment of an endodontic file or reamer 100. In particular, the file 100 is provided with a chisel tip 150, as shown in FIGS. 2B and 2C. The chisel tip 150 provides cutting ability at the tip of the instrument 100, which dramatically improves the ability of the instrument to penetrate the small opening of a calcified root canal.

The file 100 generally comprises a shaft 102 having a shank portion 104 and an elongated working portion 106. The working portion 106 extends from a proximal end 107 adjacent the base of the shank 104 to a distal end 108 terminating in a chisel tip 150. The shank portion 104 may include an optional fitting portion 109 for mating with the chuck of a dental handpiece (not shown). Alternatively, or in addition to the fitting portion 109, the shank portion 104 may include a knurled or otherwise treated surface (not shown) or handle to facilitate hand manipulation of the file 100. Those skilled in the art will appreciate that each of the endodontic instruments shown and described herein may be used by manipulating the instrument manually in a rotating or reciprocating action, or the instruments may be manipulated by attaching the shank portion of the instrument to a motorized handpiece for effecting more rapid removal of tissue from the root canal, as desired.

Figure 2D:
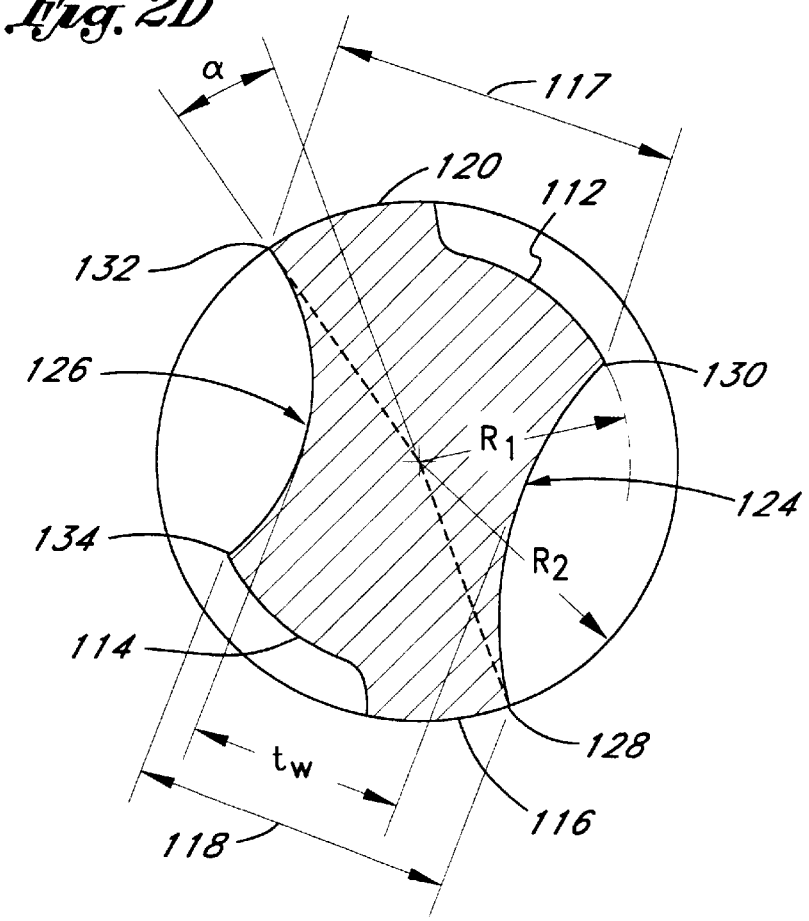
FIG. 2D is a transverse cross-section view of the reamer of FIG. 2A through a point adjacent the chisel tip.

In the particular preferred embodiment shown, the endodontic file 100 includes two helical flutes 124 and 126 formed in the working portion 106 extending from the distal end 108 adjacent the tip 150 and exiting at the proximal end 107 (sometimes called the "flute exit" or "exit"), as shown in FIGS. 2A and 2D. Those skilled in the art will readily appreciate that a similar instrument could also be configured with one flute or with three or more flutes, as desired.

Helical lands 116 and 118 are provided generally extending between adjacent flutes 124 and 126. The helical flutes 124, 126 and helical lands 116, 118 intersect one another to define leading edges 128, 132 and trailing edges 130, 134 with respect to clockwise rotation of the instrument. The leading edges 124, 126 are preferably sharp so as to remove tissue from the root canal as the instrument is rotated or reciprocated. Accordingly, these may sometimes be referred to herein as "tissue-removing" edges. The trailing edges 130, 134 may be sharp or not, depending upon the particular file geometries and manufacturing convenience.

The rake angles of the tissue-removing edges 128, 132 may be positive, negative, or neutral, as desired. Satisfactory results have been obtained with rake angles ranging from about −12 degrees to about −36 degrees measured with respect to a radial line passing through the tissue-removing edge perpendicular to a line tangent to the periphery of the working portion. The rake angles of the tissue-removing edges 128, 132 may be equal to one another or they may be different such that, for example, one may be substantially positive and another may be substantially neutral or negative. The rake angle of one or more tissue-removing edges may also vary along the length of the working portion 106, as desired, or as may be convenient for purposes of manufacturing the instruments.

Helical flutes 124, 126 may be equally sized and spaced about the periphery of the working portion 106 or, more preferably, they may be unequally sized and/or spaced about the periphery such that the curvilinear distance between tissue-removing edge 128 and tissue-removing edge 132 is different in the clockwise direction than in the counter-clockwise direction. The tissue-removing edges 128, 132 are preferably unequally spaced about the periphery of the working portion 106 by an offset angle or "clocking" angle α as shown in FIG. 2D. Unequal spacing of flutes and/or tissue-removing edges provides asymmetries in the file 100 which, according to clinical studies, significantly improve the ability of the file 100 to remove tissue evenly from the walls of a curved root canal and to more readily maintain the central axis of the canal.

The precise mechanism for the clinical improvements realized is not entirely understood at this time. But, it is believed that asymmetries in the instrument cause it, when rotated, to wander or wobble away from its rotational center, thereby more effectively contacting and cleaning out all portions of the root canal wall. Also, it is believed that due to the resulting imbalance of forces created, an asymmetric instrument will tend to cut equally aggressively on all portions of a surrounding tissue in a curved root canal than a conventional symmetric file, countering the natural tendency of a file to cut more aggressively on the inner wall at the pressure point of a file bent to conform to the shape of a curved root canal.

As shown in FIGS. 2D and 2E the helical lands 117, 118 are preferably formed so as to define outer peripheral land portions 116, 120 having width $w_1$ (sometimes referred to herein as "margin width") and recessed land portions 112, 114 having width $w_2$ (sometimes referred to herein as "relief width"), respectively. The combined width $w_1$, $w_2$ is sometimes referred to herein as "land width." The recessed land portions 112, 114 are at a first predetermined radial distance $R_1$ from the cross-sectional center of the working portion 106. The outer land portions 116, 120 lie at the outer periphery of the working portion 106 at a second predetermined radial distance $R_2$ from the center of the working portion 106, which is preferably about 4 to 30 percent greater than the radial distance $R_1$. The disclosed combination of outer and recessed land portions reduces frictional forces exerted on the instrument 100 as it is rotated within the root canal, thereby reducing overall torsional loads on the instrument.

The working portion 106 of the instrument 100 has a length ranging from about 3 mm to about 18 mm. A preferred length is about 16 mm. The working portion 106 may have a constant cross-sectional diameter or, more preferably, it is tapered from the proximal end 107 to the distal end 108, as shown. In the particular preferred embodiment shown, the taper is uniform—that is, the rate of taper is constant along the working portion 106. This taper may range from about 0.01 mm/mm to about 0.08 mm/mm and, more preferably, from about 0.02 mm/mm to about 0.06 mm/mm. The web thickness "$t_w$"—that is the thickness of the "web" of material between opposed flutes 124, 126—is also preferably tapered from the proximal end 107 of the working portion to the distal end 108. The web taper may be the same as or different from the diameter taper of the instrument. In the preferred embodiment shown the web taper may be about −0.01 mm/mm to about 0.08 mm/mm and, more preferably, is about 0.03 mm/mm. As used herein, the term "taper" or "taper rate" may refer to either the web taper rate or the diameter taper rate.

As noted above, an important feature of the instrument 100 shown in FIGS. 2A–E is the chisel tip 150, shown in more detail in FIGS. 2B and 2C. The chisel tip 150 generally comprises two or more facets 151, 153 which intersect to define a chisel edge 154. The chisel edge 154 is preferably substantially linear and substantially orthogonal to a longitudinal axis of the working portion 106, although such configuration is not necessary. Additional sharp tissue-removing edges 155, 157 are formed at the tip 150 by the intersection of the facets 151, 153 with the flutes 124, 126. Upon rotation of the instrument in a root canal the chisel edge 154 loosens diseased or decayed tissue while the tissue-removing edges 155, 157 cut away and remove the tissue as the file is inserted into the canal.

The chisel tip 150 may be formed by grinding flats or facets 151, 153 into the tip of the instrument 100, as shown, forming the chisel edge 154. The facets 151, 153 define an included point angle β of between about 45 degrees and 100 degrees, and more preferably about 60 degrees or 90 degrees, as shown in FIG. 2B. The chisel edge 154 is preferably canted from center by a primary angle γ of between about 5 and 25 degrees, and, more preferably, about 15 degrees, as shown in FIG. 2C. While a two-facet chisel tip 150 is shown and described, those skilled in the art will readily appreciate that any one of a number of multifaceted chisel tip designs may be used while enjoying the benefits and advantages of the invention as disclosed herein. For example, a four-faceted chisel tip may provide a suitable compromise for many endodontic applications.

An inherent feature of the structure shown and described above is that the facets 151, 153 of the chisel tip 150 will have apices defined by the tissue-removing edges 128, 132 and additional tissue-removing edges 155, 157 which are unequally spaced about the center of rotation of the instrument. This asymmetrical structure, in addition to providing the benefits of more even canal cutting, as described above, also creates desirable asymmetries in the chisel tip 150 of the file, giving the tip 150 a tendency to "wander" or "wobble" as the instrument is rotated in the root canal. This is particularly advantageous for extirpating a curved or convoluted root canal because the tip 150 will tend to probe around and follow the path of least resistance down the root canal, rather than make a straight path possibly through the canal wall. This feature is explained in more detail below.

FIG. 4 is a schematic free body diagram illustrating the effects of asymmetric forces exerted on the chisel tip 150. In operation, the tip is subjected to a rotational driving force represented as the moment "M". This moment produces certain reaction forces at the tip of the instrument represented by forces $F_1$ and $F_2$. Those skilled in the art will appreciate that the forces $F_1$ and $F_2$ are schematic representations of the actual forces exerted on the tip of the file which are distributed throughout the facets and edges comprising the tip 150. The simplified schematic representation of these forces is useful to illustrate the wandering dynamics of the chisel tip portion 150.

Assuming mean equilibrium conditions at the tip, the moment created by forces $F_1$ and $F_2$ acting about the rotational centerline of the file will counterbalance the moment "M" such that the two moments cancel out and the rotational speed of the tip is constant. On the other hand, due to the aforementioned asymmetries in the tip geometry, the forces $F_1$ and $F_2$, although equal in mean absolute magnitude, will not cancel out. This is because the force $F_1$ has a negative Y component that is equal to the magnitude of the force $F_1$, while the force $F_2$ has both positive X and Y components that are equal to the magnitude of the force $F_2$ multiplied by the sine and cosine of the clocking angle α, respectively. Thus, assuming the magnitudes of the forces $F_1$ and $F_2$ are equal, the net resultant force R on the tip will have an X component equal to $F_2$·(sine α) and a Y component equal to $-F_2$·(1−cos α). Of course, the magnitude and direction of the resultant force R will change with the rotation of the instrument in the root canal, thus producing the above-described wandering effect.

Desirable tip asymmetries can also be achieved in other ways, as will be readily appreciated by those skilled in the art, such as by making the rake angles of the removing edges 128, 132 different from one another and/or by dulling one of the tissue-removing edges adjacent the tip 150. The wandering chisel tip 150 combined with the ability to cut or abrade calcified material more efficiently produces an endodontic file that is faster and more efficient at cutting, while still minimizing the risk of canal transportation.

Figure 4A:
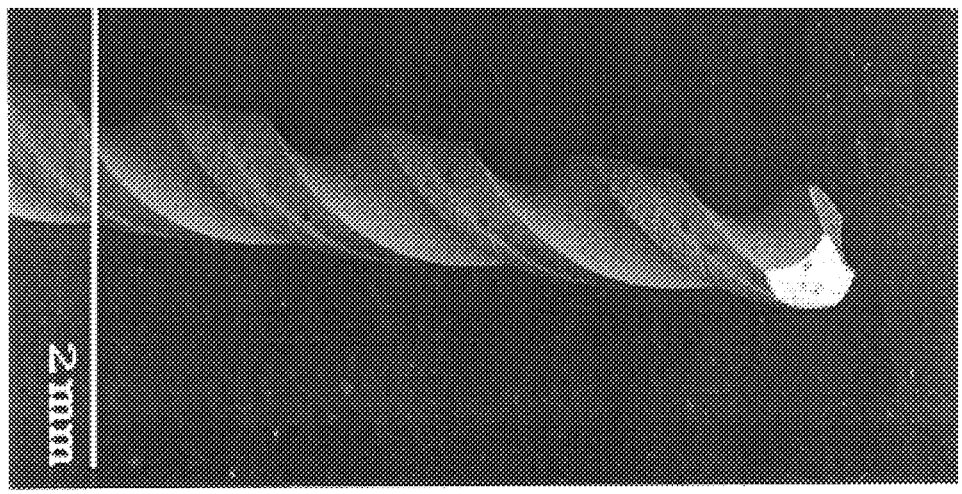
FIG. 4A is an SEM photograph (magnification 25×) of the distal end portion of an endodontic reamer including a chisel tip having features as disclosed herein.
Figure 4B:
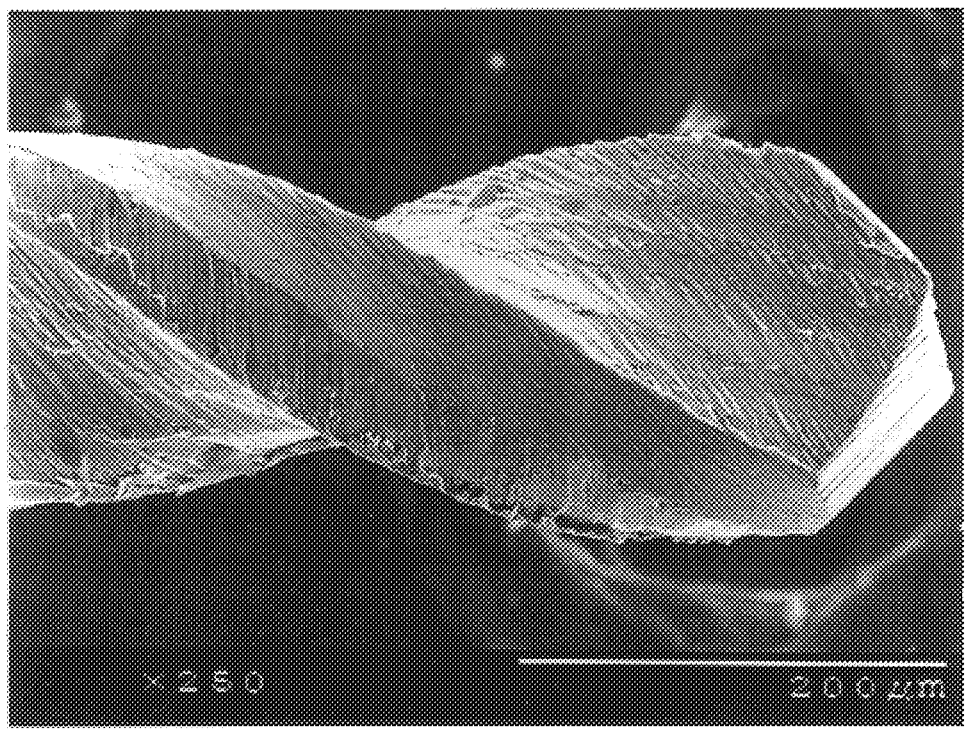
FIG. 4B is an SEM photograph (magnification 250×) of the distal end portion of an endodontic reamer including a chisel tip having features as disclosed herein.

FIGS. 4A and 4B are SEM photographs which illustrate in more detail one particular preferred embodiment of an endodontic file having a chisel tip as shown and described above. FIG. 4A is an SEM photograph of the distal end portion of an endodontic file having a chisel tip viewed at a magnification of 25×. FIG. 4B is an SEM photograph of the distal end portion of an endodontic file having a chisel tip viewed at a magnification of 250×.

FIGS. 5A–E illustrate another preferred embodiment of an endodontic file or reamer 200. This instrument is generally similar to that shown and described above in connection with FIGS. 2A–E, except that the distal end of the instrument adjacent the tip 250 has been modified to provide a region of enhanced compliance as will be described in more detail below. For convenience like reference numerals have been used to designate like structures and/or features.

The file 200 generally comprises a shaft 202 having a shank portion 204 and an elongated working portion 206. The working portion 206 has an overall length of about 3–18 mm, and, more preferably about 16 mm, and extends from a proximal end 207 adjacent the base of the shank 204 to a distal end 208 terminating in a chisel tip 250. The shank portion 204 may include an optional fitting portion 209 for mating with the chuck of a dental handpiece (not shown). Alternatively, or in addition to the fitting portion 209, the shank portion 204 may include a knurled or otherwise treated surface (not shown) or handle to facilitate hand manipulation of the file 200.

Figure 5A:
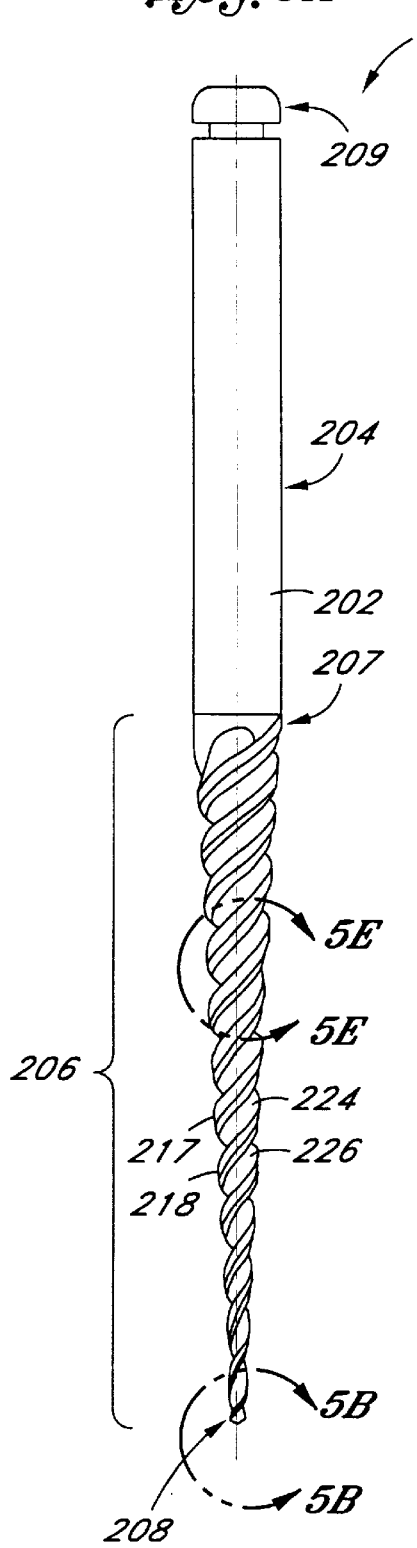
FIG. 5A is an elevational view of another embodiment an endodontic reamer instrument having an accelerated web taper.
Figure 5E:
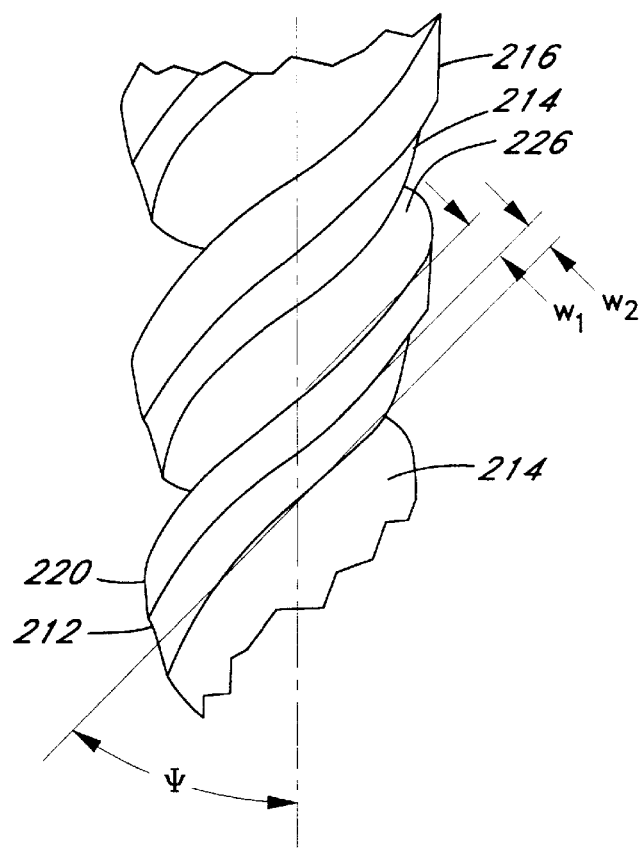
FIG. 5E is a detail side elevational view of the working portion of the reamer instrument of FIG. 5A.
Figure 5B:
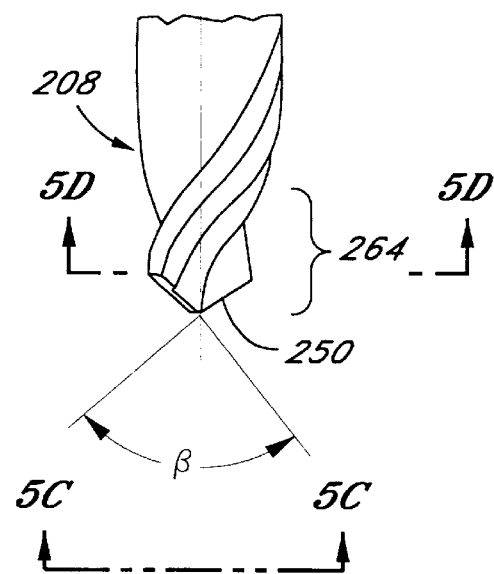
FIG. 5B is a detail side elevational view of the distal end portion of the endodontic reamer of FIG. 5A illustrating the accelerated web taper adjacent the tip of the instrument.
Figure 5C:
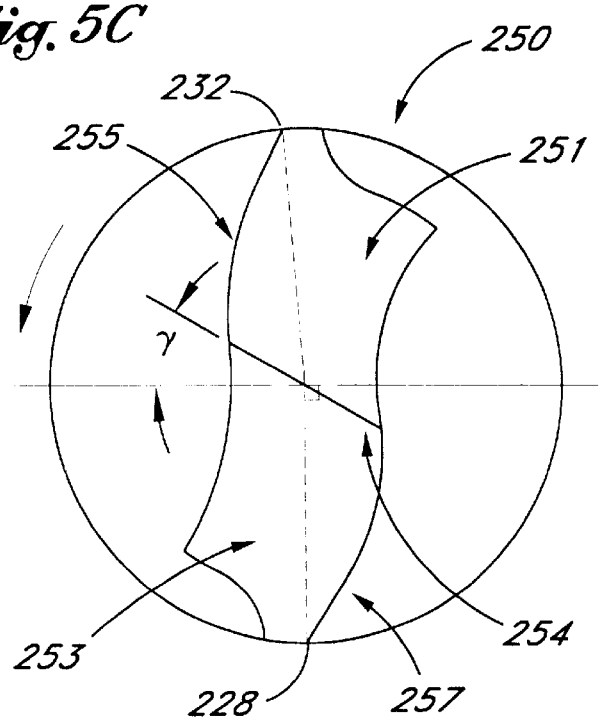
FIG. 5C is a detail end view of the tip of the endodontic reamer instrument of FIG. 5A.
Figure 5D:
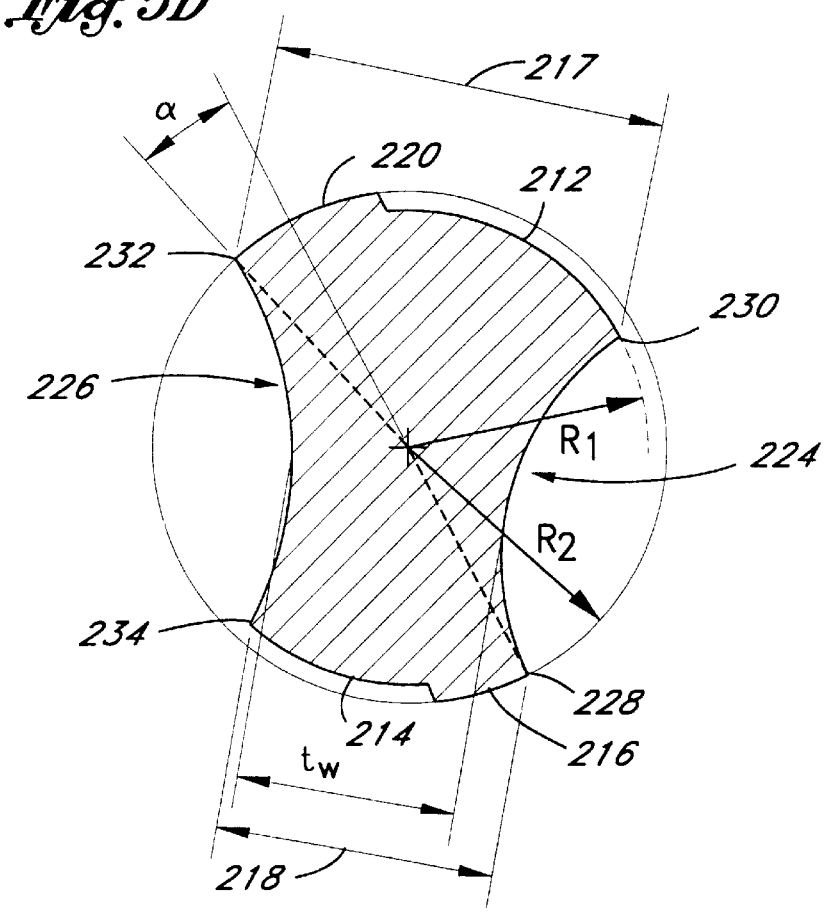
FIG. 5D is a transverse cross-section view of the reamer instrument of FIG. 5A through a point adjacent the tip.

In the particular preferred embodiment shown, the endodontic file 200 includes two helical flutes 224 and 226 and helical lands 216 and 218, as shown in FIG. 5D. The helical flutes 224, 226 and helical lands 216, 218 intersect one another to define leading edges 228, 232 and trailing edges 230, 234 with respect to clockwise rotation of the instrument. The leading edges 224, 226 are sharp so as to remove tissue from the root canal as the instrument is rotated or reciprocated. The trailing edges 230, 234 may be sharp or not, depending upon the particular design and manufacturing convenience.

The rake angles of the tissue-removing edges 228, 232 may be positive, negative, or neutral, as desired. Satisfactory results have been obtained with rake angles ranging from about −12 degrees to about −36 degrees measured with respect to a radial line passing through the tissue-removing edge perpendicular to a line tangent to the periphery of the working portion. The rake angles of the tissue-removing edges 228, 232 may be equal to one another or they may be different such that, for example, one may be substantially positive and another may be substantially neutral or negative. The rake angle of one or more tissue-removing edges may also vary along the length of the working portion 206, as desired, or as may be convenient for purposes of manufacturing the instruments.

Helical flutes 224, 226 may be equally sized and spaced about the periphery of the working portion 206 or, more preferably, they may be unequally sized and/or spaced about the periphery such that the curvilinear distance between tissue-removing edge 228 and tissue-removing edge 232 is different in the clockwise direction than in the counterclockwise direction. The tissue-removing edges 228, 232 are preferably unequally spaced about the periphery of the working portion 206 by an offset angle or "clocking" angle a as shown in FIG. 5C. As noted above, unequal spacing of flutes and/or tissue-removing edges provides asymmetries in the file 200 which improve the ability of the file 200 to remove tissue evenly from the walls of a curved root canal and to more readily maintain the central axis of the canal.

The helical lands 217, 218 are preferably formed so as to define outer peripheral land portions 216, 220 having width $w_1$ and recessed land portions 212, 214 having width $w_2$, respectively, as shown in FIGS. 5D and 5E. The recessed land portions 212, 214 are at a first predetermined radial distance $R_1$ from the cross-sectional center of the working portion 206. The outer land portions 216, 220 lie at the outer periphery of the working portion 206 at a second predetermined radial distance $R_2$ from the center of the working portion 206, which is preferably about 4 to 30 percent greater than the radial distance $R_1$. The disclosed combination of outer and recessed land portions reduces frictional forces exerted on the instrument 200 as it is rotated within the root canal, reducing overall torsional loads on the instrument.

The instrument 200 preferably has a chisel tip 250, as shown in more detail in FIGS. 5B and 5C. The chisel tip 250 generally comprises two or more facets 251, 253 which intersect to define a chisel edge 254. The chisel edge 254 is preferably substantially linear and substantially orthogonal to a longitudinal axis of the elongated working portion 206, although such configuration is not necessary. Additional sharp tissue-removing edges 255, 257 are defined at the tip by the intersection of each facet with the flutes 224, 226. Upon rotation of the instrument in a root canal the chisel edge 254 loosens the diseased or decayed tissue while the tissue-removing edges 255, 257 cut away and remove the tissue as the file is inserted into the canal.

The chisel tip 250 may be formed by grinding flats or facets 251, 253 into the tip of the instrument 200, as shown, forming the chisel edge 254. The facets 251, 253 define an included point angle β of between about 45 degrees and 100 degrees, and more preferably about 60 degrees, as shown in FIG. 5B. The chisel edge 254 is preferably canted from center by a primary angle γ of between about 5 and 25 degrees, and, more preferably, about 15 degrees, as shown in FIG. 5C. Again, while a two-facet chisel tip 250 is shown and described, those skilled in the art will readily appreciate that any one of a number of multifaceted chisel tip designs may be used while enjoying the benefits and advantages as disclosed herein.

The working portion 206 is preferably tapered from the proximal end 207 to the distal end 208, as shown. In the particular preferred embodiment shown the rate of taper is nonuniform—that is, the rate of taper (either the web taper, diameter taper or both) changes along the length of the working portion 206. In the particular embodiment shown in FIGS. 5A–E the web taper rate from a point approximately 0.02 inches from the tip 250 accelerates or increases towards the tip 250, thereby forming a region of enhanced compliance 264 adjacent the tip 250. Advantageously, this enhanced compliance region 264 enables the instrument to extirpate and enlarge a root canal more quickly and efficiently and with less tendency to transport through the canal wall than a conventional instrument of uniform taper.

Figure 6A:
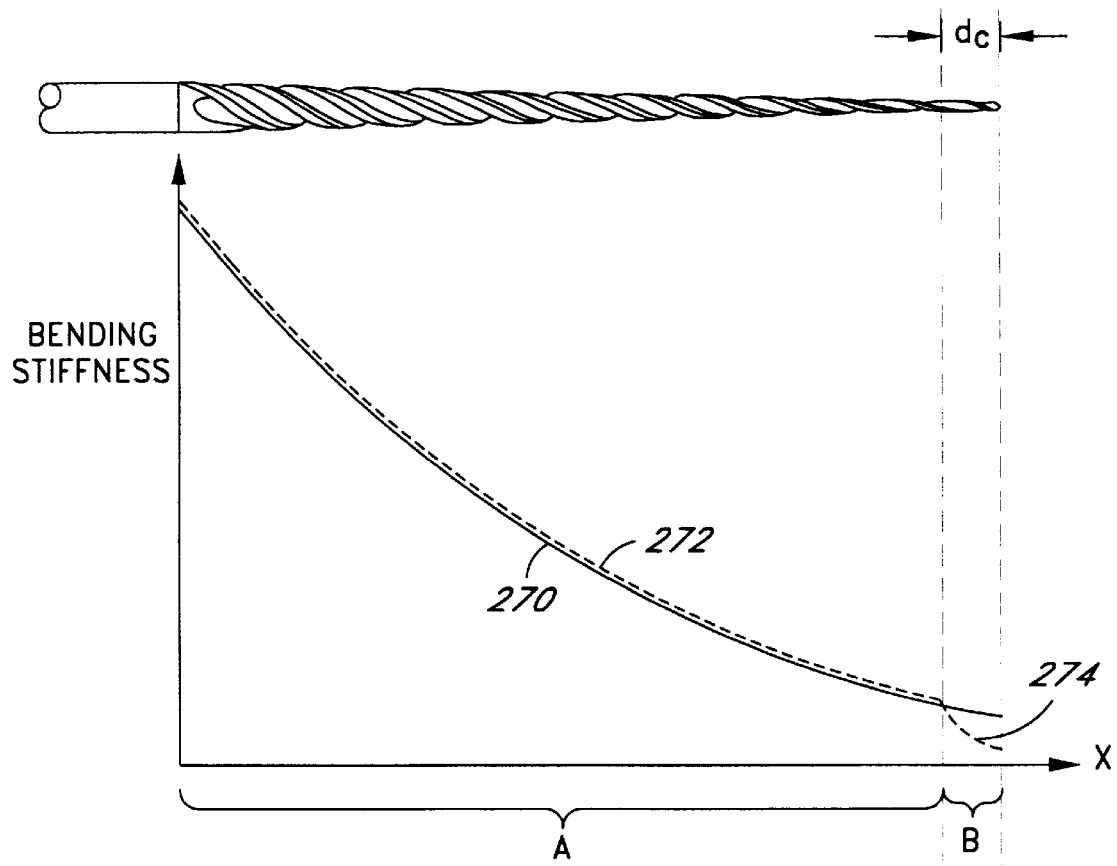
FIG. 6A is a graph of bending stiffness along the working portion of a conventional reamer instrument (shown as a solid line) as compared to the bending stiffness of a reamer instrument having features of the present invention (shown as a dashed line)
Figure 6B:
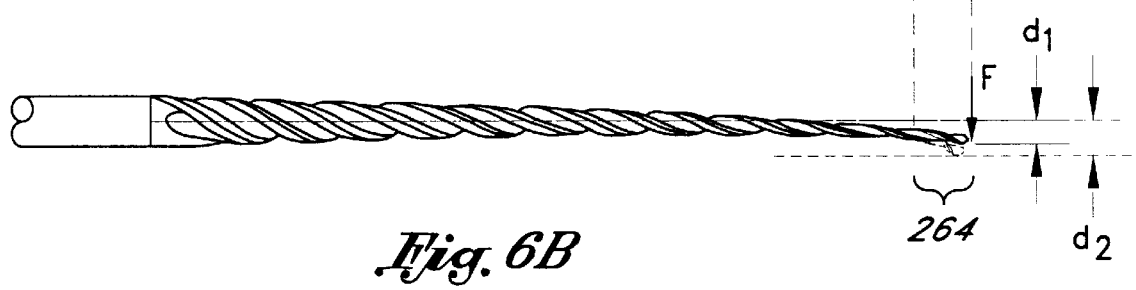
FIG. 6B is a representational schematic drawing illustrating the bending response characteristics of a conventional reamer instrument (shown in solid lines) as compared to a reamer instrument having features of the present invention (shown in dashed) when subjected to a bending force F applied at the tip.

In part, the performance improvements can be attributed to the enhanced compliance in the region 264 adjacent the tip 250, which improves the ability of the file to follow a curved root canal while simultaneously decreasing the tendency of the file to define its own path possibly through the canal wall. FIGS. 6A and 6B illustrate desired compliance characteristics of a file having the above-described features. FIG. 6A is a graph of stiffness (resistance to bending) along the working portion of a conventional file of uniform taper (shown as a solid line) as compared to the stiffness of a file constructed in accordance with the present invention and having an accelerating taper defining an enhanced compliance region adjacent the tip. The conventional tapered file will have a stiffness which decreases substantially smoothly and continuously from the proximal end of the working portion to the distal end along a single curve 270 traversing both regions A and B. In contrast, a file constructed in accordance with the present invention and having an accelerated rate of taper in the region B, as described above, will have a stiffness which decreases along a first curve 272 in the region A and then decreases along a second curve 274, which is steeper than the first curve 272, in the region B.

FIG. 6B is a representational schematic drawing illustrating the bending response characteristics of a conventional file of uniform taper (shown in solid lines) as compared to a file having an accelerated taper as described above (shown in dashed lines), subjected to a bending force F. Note that when each of the instruments is subjected to a bending force F applied at the tip of the instrument, the instrument having an accelerated taper in the region B (shown in dashed lines) will have a tip deflection $d_2$ which is greater than the tip deflection $d_1$ achieved by a conventional tapered instrument. Thus, a file constructed in accordance with the present invention will have enhanced compliance in the region 264 adjacent the tip of the instrument, resulting in the aforenoted performance improvements.

Moreover, those skilled in the art will appreciate that the compliance of such a file having an enhanced compliance region 264 in accordance with the present invention is greater than can be achieved with a conventional uniformly tapered file. To achieve the same degree of compliance adjacent the tip of a conventional tapered instrument would render the instrument unusable because it would become too compliant in the other regions of the working portion which need to be more stiff in order to withstand the torsional loads exerted on the file. The present invention, therefore, provides a unique solution by providing desired compliance characteristics adjacent the tip of an endodontic instrument without affecting desired compliance characteristics throughout the remaining portions of the instrument.

The accelerated web taper in the region 264 as shown and described above also produces a thinner web thickness two at the tip 250 and, accordingly, a shorter chisel edge 254, as illustrated in FIG. 5C (compare, eg. FIG. 2C). Advantageously, this structure results in more cutting taking place at the sharp tissue-removing edges 255, 257, rather than at the more negatively raked chisel edge 254. The tissue-removing edges 255, 257 are sharper and more efficient at cutting than the chisel edge 254. Another advantage of such structure is that the depth of the flutes 224, 226 in the region 264 are deeper, allowing more efficient removal of tissue and less friction in this region.

It should be noted that the invention as disclosed and described herein is not limited to files having an accelerated web taper. Similar enhanced compliance regions can be achieved by other means such as by providing an accelerated diameter taper in the region 264 and/or by annealing or other heat and/or chemical treating of the region 264 to produce desired localized compliance characteristics. For example, rather than accelerating the rate of web taper in the region 264 one could instead (or in addition) accelerate the rate of the diameter taper in the region 264 to achieve desired localized compliance characteristics adjacent the tip of the instrument. Providing an endodontic file with an accelerated diameter taper could also have additional advantages, such as reducing the tip diameter of the instrument so as to allow it to more easily enter and enlarge small root canal openings. Alternatively, a combination of these techniques would be used.

It should also be noted that while the preferred embodiments shown and described in connection with FIGS. 5A–E illustrate the particular desirability of providing an accelerated taper in the region 264 adjacent the tip of the instrument, a wide variety of other configurations are also possible. The accelerating taper can be either a localized effect or it can extend the entire length of the working portion of the instrument, if desired. Moreover, the change in taper rate can be either graduated or substantially instantaneous, as desired. These and other embodiments of the present invention will be readily apparent to those persons skilled in the art.

Figure 7A:
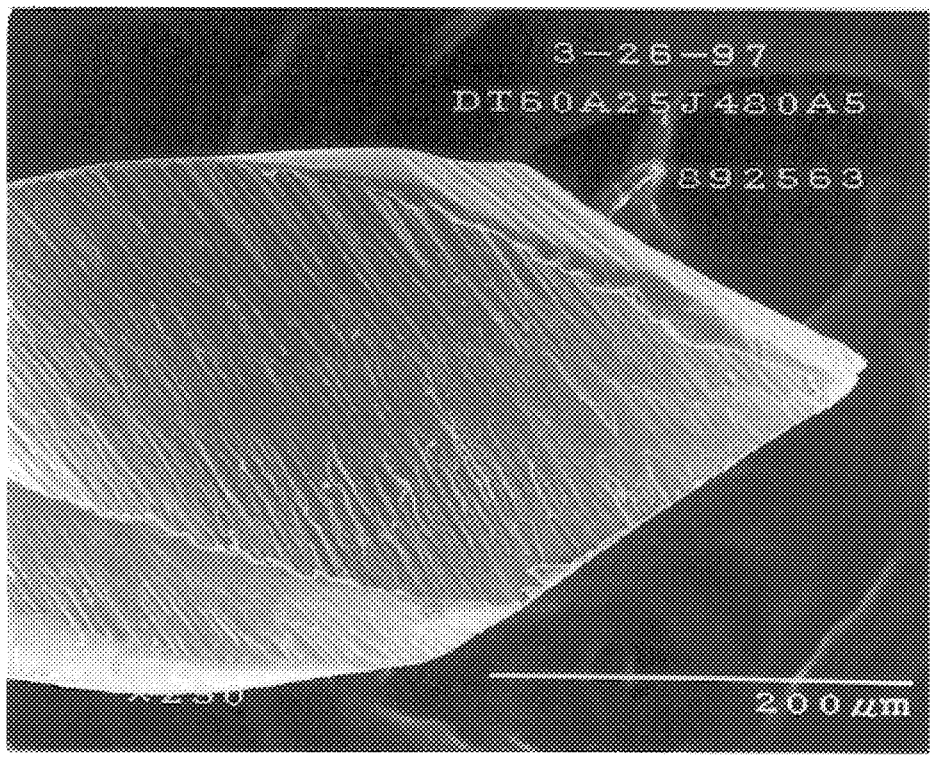
FIG. 7A is an SEM photograph (magnification 250×) of the distal end portion of an endodontic reamer having features as disclosed herein.
Figure 7B:
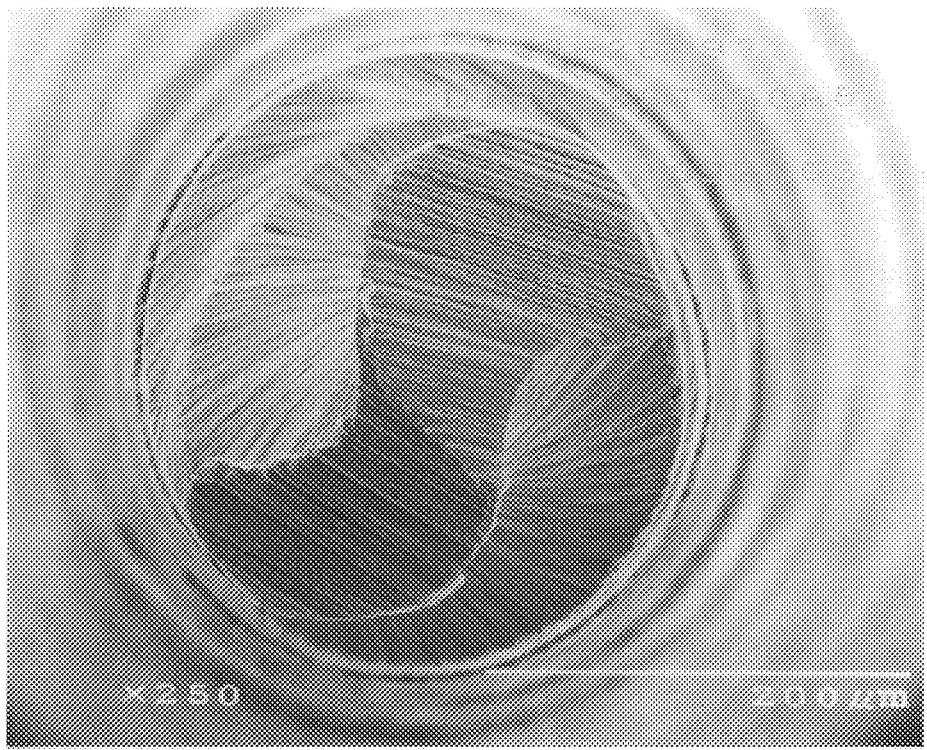
FIG. 7B is an SEM photograph (magnification 250×) of the tip of an endodontic reamer having features as disclosed herein.

FIGS. 7A and 7B are SEM photographs which illustrate in more detail one particular preferred embodiment of an endodontic file having an accelerated web taper in a region adjacent the tip as shown and described above. FIG. 7A is an SEM photograph of the distal end portion of such an endodontic file viewed at a magnification of 25×. FIG. 7B is an SEM photograph of the distal end portion of such an endodontic file viewed at a magnification of 250×.

The endodontic instruments in accordance with the preferred embodiments described above are preferably made from a strong, highly elastic material such as nickel-titanium, Nitinol™ or other suitable alloy. They can also be made from surgical stainless steel, if desired. A particularly preferred material is titanium 13—13 or a nickel-titanium alloy comprising about 56% nickel and about 44% titanium, such as SE508 nickel-titanium wire available from Nitinol Devices and Components, Inc. of Fremont, Calif.

Those skilled in the art will recognize that any one of a variety of well known techniques for making conventional instruments may generally be applied to the manufacture of instruments as disclosed herein with various known or later developed improvements in materials or processing. For example, the instruments may be ground from a straight or tapered rod, twisted, and/or drawn to a taper with or without grinding. Suitable grinding techniques which may be used are described in standard metallurgical texts for grinding various metals.

The following examples provide preferred specifications, dimensions and fabrication techniques for producing various preferred embodiments of endodontic files having features and advantages as disclosed herein. All dimensions are in inches unless otherwise noted.

EXAMPLE 1

The following instrument was formed from a tapered blank of SE508 nickel-titanium wire having a substantially uniformly tapered outer diameter and a substantially uniform web taper. This particular instrument has two helical flutes (denoted flute "A" and flute "B") of unequal size and spaced unevenly around the periphery of the instrument. The flutes were formed by grinding the blank with a 320 grit CBN grinding wheel at a grinding speed of about 9,000 SFPM and an axial feed rate of about 2 inches/min.

|  | NOMINAL | PLUS | MINUS |
| --- | --- | --- | --- |
| DIAMETER AT TIP | 0.0098 | 0.0004 | 0.0004 |
| DIAMETER TAPER RATE | 0.050 | | |
| SHANK DIAMETER | 0.0413 | 0.0003 | 0.0003 |
| FLUTE LENGTH | 0.6300 | 0.0100 | 0.0100 |
| RELIEF LENGTH | 0.6300 | 0.0100 | 0.0100 |
| HELIX ANGLE (Ψ) @ TIP | 30° | 1° | 1° |
| HELIX ANGLE (Ψ) @ EXIT | 45° | 1° | 1° |
| WEB THICKNESS @ TIP | 0.0029 | 0.0006 | 0.0006 |
| LAND WIDTH @ TIP | 0.0053 | 0.0004 | 0.0004 |
| LAND WIDTH @ EXIT | 0.0275 | 0.0004 | 0.0004 |
| RELIEF DIAMETER @ TIP | 0.0078 | 0.0008 | 0.0008 |
| MARGIN WIDTH @ TIP | 0.0019 | 0.0004 | 0.0004 |
| MARGIN WIDTH @ EXIT | 0.0128 | 0.0004 | 0.0004 |
| WEB TAPER RATE @ TIP | 0.0300 | 0.0040 | 0.0040 |
| WEB TAPER RATE @ EXIT | 0.0300 | 0.0040 | 0.0040 |

-continued

|  | NOMINAL | PLUS | MINUS |
|---|---|---|---|
| POINT ANGLE (β) | 90° | 2° | 2° |
| PRIMARY ANGLE (γ) | 15° | 1° | 1° |
| CLOCKING ANGLE (α) | 175° | 1° | 1° |
| OVERALL LENGTH | 1.2000 | 0.0010 | 0.0010 |
| REFERENCE DIMENSIONS ONLY | | | |
| RAKE ANGLE FLUTE A @ TIP | 14° | | |
| RAKE ANGLE FLUTE B @ TIP | −10° | | |
| RAKE ANGLE FLUTE A @ EXIT | −34° | | |
| RAKE ANGLE FLUTE B @ EXIT | −35° | | |

EXAMPLE 2

The following instrument was formed from a tapered blank of SE508 nickel-titanium wire having a substantially uniformly tapered outer diameter and a non-uniformly tapered web. This particular instrument has two helical flutes of approximately equal size and shape and which are unequally spaced around the periphery of the instrument. The flutes were formed by grinding the blank with a 600 grit diamond grinding wheel at a grinding speed of 6,311 SFPM and an axial feed rate of 1.95 inches/min.

|  | NOMINAL | PLUS | MINUS |
|---|---|---|---|
| DIAMETER AT TIP | 0.0157 | 0.0003 | 0.0003 |
| DIAMETER TAPER RATE | 0.020 | 0.001 | 0.001 |
| SHANK DIAMETER | 0.0285 | 0.0003 | 0.0003 |
| FLUTE LENGTH | 0.630 | 0.010 | 0.010 |
| RELIEF LENGTH | 0.630 | 0.010 | 0.010 |
| HELIX ANGLE (Ψ) @ TIP | 30° | 1° | 1° |
| HELIX ANGLE (Ψ) @ EXIT | 45° | 1° | 1° |
| NUMBER OF FLUTES IN .630 | 13 | | |
| WEB THICKNESS @ TIP | 0.0029 | 0.0010 | 0.0010 |
| RELIEF DIAMETER @ TIP | 0.0122 | 0.0010 | 0.0010 |
| LAND WIDTH 1 @ TIP | 0.0081 | 0.0008 | 0.0008 |
| LAND WIDTH 2 @ TIP | 0.0097 | 0.0008 | 0.0008 |
| LAND WIDTH 1 @ EXIT | 0.0150 | 0.0008 | 0.0008 |
| LAND WIDTH 2 @ EXIT | 0.0178 | 0.0008 | 0.0008 |
| MARGIN WIDTH 1 @ TIP | 0.0034 | 0.0008 | 0.0008 |
| MARGIN WIDTH 2 @ TIP | 0.0031 | 0.0008 | 0.0008 |
| MARGIN WIDTH 1 @ EXIT | 0.0078 | 0.0008 | 0.0008 |
| MARGIN WIDTH 2 @ EXIT | 0.0076 | 0.0008 | 0.0008 |
| WEB THICKNESS @ .02 FROM TIP | 0.0051 | 0.0010 | 0.0010 |
| WEB TAPER RATE (TIP TO .02) | 0.110 | 0.002 | 0.002 |
| WEB TAPER RATE (.02 TO EXIT) | 0.020 | 0.002 | 0.002 |
| POINT ANGLE (β) | 60° | 2° | 2° |
| PRIMARY ANGLE (γ) | 15° | 2° | 2° |
| CLOCKING ANGLE (α) | 170° | 2° | 2° |
| OVERALL LENGTH | 1.500 | 0.003 | 0.003 |
| REFERENCE DIMENSIONS ONLY | | | |
| RAKE ANGLE @ TIP | −12° | 2° | 2° |
| RAKE ANGLE @ EXIT | ≧−15° | | |

EXAMPLE 3

The following instrument was formed from a tapered blank of SE508 nickel-titanium wire having a substantially uniformly tapered outer diameter and a non-uniformly tapered web. This particular instrument has two helical flutes of approximately equal size and shape and which are unequally spaced around the periphery of the instrument. The flutes were formed by grinding the blank with a 320/400 grit CBN grinding wheel at a grinding speed of 9,579 SFPM and an axial feed rate of 1.70 inches/min.

|  | NOMINAL | PLUS | MINUS |
|---|---|---|---|
| DIAMETER AT TIP | 0.0177 | 0.0003 | 0.0003 |
| DIAMTER TAPER RATE | 0.020 | 0.001 | 0.001 |
| SHANK DIAMETER | 0.0300 | 0.0003 | 0.0003 |
| FLUTE LENGTH | 0.630 | 0.010 | 0.010 |
| RELIEF LENGTH | 0.630 | 0.010 | 0.010 |
| HELIX ANGLE (Ψ) @ TIP | 30° | 1° | 1° |
| HELIX ANGLE (Ψ) @ EXIT | 45° | 1° | 1° |
| NUMBER OF FLUTES IN .630 | 12 | | |
| WEB THICKNESS @ TIP | 0.0033 | 0.0010 | 0.0010 |
| RELIEF DIAMETER @ TIP | 0.0140 | 0.0010 | 0.0010 |
| LAND WIDTH 1 @ TIP | 0.0104 | 0.0008 | 0.0008 |
| LAND WIDTH 2 @ TIP | 0.0097 | 0.0008 | 0.0008 |
| LAND WIDTH 1 @ EXIT | 0.0168 | 0.0008 | 0.0008 |
| LAND WIDTH 2 @ EXIT | 0.0193 | 0.0008 | 0.0008 |
| MARGIN WIDTH 1 @ TIP | 0.0055 | 0.0008 | 0.0008 |
| MARGIN WIDTH 2 @ TIP | 0.0053 | 0.0008 | 0.0008 |
| MARGIN WIDTH 1 @ EXIT | 0.0101 | 0.0008 | 0.0008 |
| MARGIN WIDTH 2 @ EXIT | 0.0102 | 0.0008 | 0.0008 |
| WEB THICKNESS @ .02 FROM TIP | 0.0057 | 0.0010 | 0.0010 |
| WEB TAPER RATE (TIP TO .02) | 0.121 | 0.002 | 0.002 |
| WEB TAPER RATE (.02 TO EXIT) | 0.020 | 0.002 | 0.002 |
| POINT ANGLE (β) | 60° | 2° | 2° |
| PRIMARY ANGLE (γ) | 15° | 2° | 2° |
| CLOCKING ANGLE (α) | 170° | 2° | 2° |
| OVERALL LENGTH | 1.500 | 0.003 | 0.003 |
| REFERENCE DIMENSIONS ONLY | | | |
| RAKE ANGLE @ TIP | −12° | 2° | 2° |
| RAKE ANGLE @ EXIT | ≧−15° | | |

EXAMPLE 4

The following instrument was formed from a tapered blank of SE508 nickel-titanium wire having a substantially uniformly tapered outer diameter and a non-uniformly tapered web. This particular instrument has two helical flutes of approximately equal size and shape and which are unequally spaced around the periphery of the instrument. The flutes were formed by grinding the blank with a 600 grit diamond grinding wheel at a grinding speed of about 9,000 SFPM and an axial feed rate of 1.70 inches/min.

|  | NOMINAL | PLUS | MINUS |
|---|---|---|---|
| DIAMETER AT TIP | 0.0098 | 0.0003 | 0.0003 |
| DIAMETER TAPER RATE | 0.030 | 0.001 | 0.001 |
| SHANK DIAMETER | 0.0285 | 0.0003 | 0.0003 |
| FLUTE LENGTH | 0.630 | 0.010 | 0.010 |
| RELIEF LENGTH | 0.630 | 0.010 | 0.010 |
| HELIX ANGLE (Ψ) @ TIP | 30° | 1° | 1° |
| HELIX ANGLE (Ψ) @ EXIT | 45° | 1° | 1° |
| NUMBER OF FLUTES IN .630 | 16 | | |
| WEB THICKNESS @ TIP | 0.0018 | 0.0010 | 0.0010 |
| RELIEF DIAMETER @ TIP | 0.0070 | 0.0010 | 0.0010 |
| LAND WIDTH 1 @ TIP | 0.0059 | 0.0008 | 0.0008 |
| LAND WIDTH 2 @ TIP | 0.0063 | 0.0008 | 0.0008 |
| LAND WIDTH 1 @ EXIT | 0.0148 | 0.0008 | 0.0008 |
| LAND WIDTH 2 @ EXIT | 0.0165 | 0.0008 | 0.0008 |
| MARGIN WIDTH 1 @ TIP | 0.0019 | 0.0008 | 0.0008 |
| MARGIN WIDTH 2 @ TIP | 0.0025 | 0.0008 | 0.0008 |
| MARGIN WIDTH 1 @ EXIT | 0.0072 | 0.0008 | 0.0008 |
| MARGIN WIDTH 2 @ EXIT | 0.0068 | 0.0008 | 0.0008 |
| WEB THICKNESS @ FROM TIP | 0.0050 | 0.0010 | 0.0010 |
| WEB TAPER RATE (TIP TO .02) | 0.160 | 0.002 | 0.002 |
| WEB TAPER RATE (.02 TO EXIT) | 0.03 | 0.002 | 0.002 |
| POINT ANGLE (β) | 60° | 2° | 2° |
| PRIMARY ANGLE (γ) | 15° | 2° | 2° |
| CLOCKING ANGLE (α) | 170° | 2° | 2° |
| OVERALL LENGTH | 1.500 | 0.003 | 0.003 |

-continued

|  | NOMINAL | PLUS | MINUS |
|---|---|---|---|
| REFERENCE DIMENSIONS ONLY ||||
| RAKE ANGLE @ TIP | −16° | 2° | 2° |
| RAKE ANGLE @ EXIT | ≧−15° | | |

EXAMPLE 5

The following instrument was formed from a tapered blank of SE508 nickel-titanium wire having a substantially uniformly tapered outer diameter and a non-uniformly tapered web. This particular instrument has two helical flutes of approximately equal size and shape and which are unequally spaced around the periphery of the instrument. The flutes were formed by grinding the blank with a 600 grit diamond grinding wheel at a grinding speed of 9,078 SFPM and an axial feed rate of 2.17 inches/min.

|  | NOMINAL | PLUS | MINUS |
|---|---|---|---|
| DIAMETER AT TIP | 0.0098 | 0.0003 | 0.0003 |
| DIAMETER TAPER RATE | 0.040 | 0.001 | 0.001 |
| SHANK DIAMETER | 0.0350 | 0.0003 | 0.0003 |
| FLUTE LENGTH | 0.630 | 0.010 | 0.010 |
| RELIEF LENGTH | 0.630 | 0.010 | 0.010 |
| HELIX ANGLE (Ψ) @ TIP | 30° | 1° | 1° |
| HELIX ANGLE (Ψ) @ EXIT | 45° | 1° | 1° |
| NUMBER OF FLUTES IN .630 | 15 | | |
| WEB THICKNESS @ TIP | 0.0018 | 0.0010 | 0.0010 |
| RELIEF DIAMETER @ TIP | 0.0070 | 0.0010 | 0.0010 |
| LAND WIDTH 1 @ TIP | 0.0056 | 0.0008 | 0.0008 |
| LAND WIDTH 2 @ TIP | 0.0074 | 0.0008 | 0.0008 |
| LAND WIDTH 1 @ EXIT | 0.0206 | 0.0008 | 0.0008 |
| LAND WIDTH 2 @ EXIT | 0.0214 | 0.0008 | 0.0008 |
| MARGIN WIDTH 1 @ TIP | 0.0031 | 0.0008 | 0.0008 |
| MARGIN WIDTH 2 @ TIP | 0.0037 | 0.0008 | 0.0008 |
| MARGIN WIDTH 1 @ EXIT | 0.0132 | 0.0008 | 0.0008 |
| MARGIN WIDTH 2 @ EXIT | 0.0121 | 0.0008 | 0.0008 |
| WEB THICKNESS @ .02 FROM TIP | 0.0048 | 0.0010 | 0.0010 |
| WEB TAPER RATE (TIP TO .02) | 0.150 | 0.002 | 0.002 |
| WEB TAPER RATE (.02 TO EXIT) | 0.02 | 0.002 | 0.002 |
| POINT ANGLE (β) | 60° | 2° | 2° |
| PRIMARY ANGLE (γ) | 15° | 2° | 2° |
| CLOCKING ANGLE (α) | 170° | 2° | 2° |
| OVERALL LENGTH | 1.500 | 0.003 | 0.003 |
| REFERENCE DIMENSIONS ONLY ||||
| RAKE ANGLE @ TIP | −16° | 2° | 2° |
| RAKE ANGLE @ EXIT | ≧−15° | | |

EXAMPLE 6

The following instrument was formed from a tapered blank of SE508 nickel-titanium wire having a substantially uniformly tapered outer diameter and a non-uniformly tapered web. This particular instrument has two helical flutes of approximately equal size and shape and which are unequally spaced around the periphery of the instrument. The flutes were formed by grinding the blank with a 320 grit CBN grinding wheel at a grinding speed of 8,963 SFPM and an axial feed rate of 1.95 inches/min.

|  | NOMINAL | PLUS | MINUS |
|---|---|---|---|
| DIAMETER AT TIP | 0.0098 | 0.0003 | 0.0003 |
| DIAMETER TAPER RATE | 0.050 | 0.001 | 0.001 |
| SHANK DIAMETER | 0.0410 | 0.0003 | 0.0003 |
| FLUTE LENGTH | 0.630 | 0.010 | 0.010 |
| RELIEF LENGTH | 0.630 | 0.010 | 0.010 |
| HELIX ANGLE (Ψ) @ TIP | 30° | 1° | 1° |
| HELIX ANGLE (Ψ) @ EXIT | 45° | 1° | 1° |
| NUMBER OF FLUTES IN .630 | 13 | | |
| WEB THICKNESS @ TIP | 0.0018 | 0.0010 | 0.0010 |
| RELIEF DIAMETER @ TIP | 0.0070 | 0.0010 | 0.0010 |
| LAND WIDTH 1 @ TIP | 0.0060 | 0.0008 | 0.0008 |
| LAND WIDTH 2 @ TIP | 0.0078 | 0.0008 | 0.0008 |
| LAND WIDTH 1 @ EXIT | 0.0245 | 0.0008 | 0.0008 |
| LAND WIDTH 2 @ EXIT | 0.0267 | 0.0008 | 0.0008 |
| MARGIN WIDTH 1 @ TIP | 0.0029 | 0.0008 | 0.0008 |
| MARGIN WIDTH 2 @ TIP | 0.0039 | 0.0008 | 0.0008 |
| MARGIN WIDTH 1 @ EXIT | 0.0153 | 0.0008 | 0.0008 |
| MARGIN WIDTH 2 @ EXIT | 0.0146 | 0.0008 | 0.0008 |
| WEB THICKNESS @ .02 FROM TIP | 0.0052 | 0.0002 | 0.0002 |
| WEB TAPER RATE (TIP TO .02) | 0.170 | 0.002 | 0.002 |
| WEB TAPER RATE (.02 TO EXIT) | 0.04 | 0.002 | 0.002 |
| POINT ANGLE (β) | 60° | 2° | 2° |
| PRIMARY ANGLE (γ) | 15° | 2° | 2° |
| CLOCKING ANGLE (α) | 170° | 2° | 2° |
| OVERALL LENGTH | 1.500 | 0.003 | 0.003 |
| REFERENCE DIMENSIONS ONLY ||||
| RAKE ANGLE @ TIP | −16° | 2° | 2° |
| RAKE ANGLE @ EXIT | ≧−15° | | |

EXAMPLE 7

The following instrument was formed from a tapered blank of SE508 nickel-titanium wire having a substantially uniformly tapered outer diameter and a non-uniformly tapered web. This particular instrument has two helical flutes of approximately equal size and shape and which are unequally spaced around the periphery of the instrument. The flutes were formed by grinding the blank with a 600 grit diamond grinding wheel at a grinding speed of 8,898 SFPM and an axial feed rate of 1.70 inches/min.

|  | NOMINAL | PLUS | MINUS |
|---|---|---|---|
| DIAMETER AT TIP | 0.0098 | 0.0003 | 0.0003 |
| DIAMETER TAPER RATE | 0.060 | 0.001 | 0.001 |
| SHANK DIAMETER | 0.0480 | 0.0003 | 0.0003 |
| FLUTE LENGTH | 0.630 | 0.010 | 0.010 |
| RELIEF LENGTH | 0.630 | 0.010 | 0.010 |
| HELIX ANGLE (Ψ) @ TIP | 30° | 1° | 1° |
| HELIX ANGLE (Ψ) @ EXIT | 45° | 1° | 1° |
| NUMBER OF FLUTES IN .630 | 12 | | |
| WEB THICKNESS @ TIP | 0.0018 | 0.0010 | 0.0010 |
| RELIEF DIAMETER @ TIP | 0.0065 | 0.0010 | 0.0010 |
| LAND WIDTH 1 @ TIP | 0.0056 | 0.0008 | 0.0008 |
| LAND WIDTH 2 @ TIP | 0.0064 | 0.0008 | 0.0008 |
| LAND WIDTH 1 @ EXIT | 0.0170 | 0.0008 | 0.0008 |
| LAND WIDTH 2 @ EXIT | 0.0207 | 0.0008 | 0.0008 |
| MARGIN WIDTH 1 @ TIP | 0.0034 | 0.0008 | 0.0008 |
| MARGIN WIDTH 2 @ TIP | 0.0040 | 0.0008 | 0.0008 |
| MARGIN WIDTH 1 @ EXIT | 0.0076 | 0.0008 | 0.0008 |
| MARGIN WIDTH 2 @ EXIT | 0.0078 | 0.0008 | 0.0008 |
| WEB THICKNESS @ .02 FROM TIP | 0.0039 | 0.0002 | 0.0002 |
| WEB TAPER RATE (TIP TO .02) | 0.105 | 0.002 | 0.002 |
| WEB TAPER RATE (.02 TO EXIT) | 0.024 | 0.002 | 0.002 |
| POINT ANGLE (β) | 60° | 2° | 2° |
| PRIMARY ANGLE (γ) | 15° | 2° | 2° |
| CLOCKING ANGLE (α) | 170° | 2° | 2° |
| OVERALL LENGTH | 1.500 | 0.003 | 0.003 |
| REFERENCE DIMENSIONS ONLY ||||
| RAKE ANGLE @ TIP | −16° | 2° | 2° |
| RAKE ANGLE @ EXIT | ≧−15° | | |

EXAMPLE 8

The following instrument was formed from a tapered blank of SE508 nickel-titanium wire having a substantially uniformly tapered outer diameter and a non-uniformly tapered web. This particular instrument has two helical flutes of approximately equal size and shape and which are unequally spaced around the periphery of the instrument. The flutes were formed by grinding the blank with a 600 grit diamond grinding wheel at a grinding speed of 8,980 SFPM and an axial feed rate of 1.30 inches/min.

| | NOMINAL | PLUS | MINUS |
|---|---|---|---|
| DIAMETER AT TIP | 0.0059 | 0.0003 | 0.0003 |
| DIAMETER TAPER RATE | 0.020 | 0.001 | 0.001 |
| SHANK DIAMETER | 0.0185 | 0.0003 | 0.0003 |
| FLUTE LENGTH | 0.630 | 0.010 | 0.010 |
| RELIEF LENGTH | 0.630 | 0.010 | 0.010 |
| HELIX ANGLE ($\Psi$) @ TIP | 30° | 1° | 1° |
| HELIX ANGLE ($\Psi$) @ EXIT | 45° | 1° | 1° |
| NUMBER OF FLUTES IN .630 | 27 | | |
| WEB THICKNESS @ TIP | 0.0011 | 0.0010 | 0.0010 |
| RELIEF DIAMETER @ TIP | 0.0045 | 0.0010 | 0.0010 |
| LAND WIDTH 1 @ TIP | 0.0032 | 0.0008 | 0.0008 |
| LAND WIDTH 2 @ TIP | 0.0041 | 0.0008 | 0.0008 |
| LAND WIDTH 1 @ EXIT | 0.0099 | 0.0008 | 0.0008 |
| LAND WIDTH 2 @ EXIT | 0.0116 | 0.0008 | 0.0008 |
| MARGIN WIDTH 1 @ TIP | 0.0014 | 0.0008 | 0.0008 |
| MARGIN WIDTH 2 @ TIP | 0.0017 | 0.0008 | 0.0008 |
| MARGIN WIDTH 1 @ EXIT | 0.0039 | 0.0008 | 0.0008 |
| MARGIN WIDTH 2 @ EXIT | 0.0039 | 0.0008 | 0.0008 |
| WEB THICKNESS @ .02 FROM TIP | 0.0039 | 0.0010 | 0.0010 |
| WEB TAPER RATE (TIP TO .02) | 0.141 | 0.002 | 0.002 |
| WEB TAPER RATE (.02 TO EXIT) | 0.019 | 0.002 | 0.002 |
| POINT ANGLE ($\beta$) | 60° | 2° | 2° |
| PRIMARY ANGLE ($\gamma$) | 15° | 2° | 2° |
| CLOCKING ANGLE $\alpha$ | 170° | 2° | 2° |
| OVERALL LENGTH | 1.500 | 0.003 | 0.003 |
| REFERENCE DIMENSIONS ONLY | | | |
| RAKE ANGLE @ TIP | −12° | 2° | 2° |
| RAKE ANGLE @ EXIT | $\geq$−15° | | |

EXAMPLE 9

The following instrument was formed from a tapered blank of SE508 nickel-titanium wire having a substantially uniformly tapered outer diameter and a non-uniformly tapered web. This particular instrument has two helical flutes of approximately equal size and shape and which are unequally spaced around the periphery of the instrument. The flutes were formed by grinding the blank with a 600 grit diamond grinding wheel at a grinding speed of 8,909 SFPM and an axial feed rate of 1.70 inches/min.

| | NOMINAL | PLUS | MINUS |
|---|---|---|---|
| DIAMETER AT TIP | 0.0079 | 0.0003 | 0.0003 |
| DIAMETER TAPER RATE | 0.020 | 0.001 | 0.00I |
| SHANK DIAMETER | 0.0205 | 0.0003 | 0.0003 |
| FLUTE LENGTH | 0.630 | 0.010 | 0.010 |
| RELIEF LENGTH | 0.630 | 0.010 | 0.010 |
| HELIX ANGLE ($\Psi$) @ TIP | 30° | 1° | 1° |
| HELIX ANGLE ($\Psi$) @ EXIT | 45° | 1° | 1° |
| NUMBER OF FLUTES IN .630 | 22 | | |
| WEB THICKNESS @ TIP | 0.0015 | 0.0010 | 0.0010 |
| RELIEF DIAMETER @ TIP | 0.0067 | 0.0010 | 0.0010 |
| LAND WIDTH 1 @ TIP | 0.0032 | 0.0008 | 0.0008 |
| LAND WIDTH 2 @ TIP | 0.0035 | 0.0008 | 0.0008 |
| LAND WIDTH 1 @ EXIT | 0.0105 | 0.0008 | 0.0008 |
| LAND WIDTH 2 @ EXIT | 0.0125 | 0.0008 | 0.0008 |
| MARGIN WIDTH 1 @ TIP | 0.0011 | 0.0008 | 0.0008 |
| MARGIN WIDTH 2 @ TIP | 0.0011 | 0.0008 | 0.0008 |
| MARGIN WIDTH 1 @ EXIT | 0.0065 | 0.0008 | 0.0008 |
| MARGIN WIDTH 2 @ EXIT | 0.0068 | 0.0008 | 0.0008 |
| WEB THICKNESS @ .02 TIP | 0.0051 | 0.0002 | 0.0002 |
| WEB TAPER RATE (TIP TO .02) | 0.182 | 0.002 | 0.002 |
| WEB TAPER RATE (.02 TO EXIT) | 0.019 | 0.002 | 0.002 |
| POINT ANGLE ($\beta$) | 60° | 2° | 2° |
| PRIMARY ANGLE ($\gamma$) | 15° | 2° | 2° |
| CLOCKING ANGLE ($\alpha$) | 170° | 2° | 2° |
| OVERALL LENGTH | 1.500 | 0.003 | 0.003 |
| REFERENCE DIMENSIONS ONLY | | | |
| RAKE ANGLE @ TIP | −12° | 2° | 2° |
| RAKE ANGLE @ EXIT | $\geq$−15° | | |

EXAMPLE 10

The following instrument was formed from a tapered blank of SE508 nickel-titanium wire having a substantially uniformly tapered outer diameter and a non-uniformly tapered web. This particular instrument has two helical flutes of approximately equal size and shape and which are unequally spaced around the periphery of the instrument. The flutes were formed by grinding the blank with a 600 grit diamond grinding wheel at a grinding speed of 8,963 SFPM and an axial feed rate of 1.56 inches/min.

| | NOMINAL | PLUS | MINUS |
|---|---|---|---|
| DIAMETER AT TIP | 0.0098 | 0.0003 | 0.0003 |
| DIAMETER TAPER RATE | 0.020 | 0.001 | 0.001 |
| SHANK DIAMETER | 0.0225 | 0.0003 | 0.0003 |
| FLUTE LENGTH | 0.630 | 0.010 | 0.010 |
| RELIEF LENGTH | 0.630 | 0.010 | 0.010 |
| HELIX ANGLE ($\Psi$) @ TIP | 30° | 1° | 1° |
| HELIX ANGLE ($\Psi$) @ EXIT | 45° | 1° | 1° |
| NUMBER OF FLUTES IN .630 | 20 | | |
| WEB THICKNESS @ TIP | 0.0018 | 0.0010 | 0.0010 |
| RELIEF DIAMETER @ TIP | 0.0063 | 0.0010 | 0.0010 |
| LAND WIDTH 1 @ TIP | 0.0044 | 0.0008 | 0.0008 |
| LAND WIDTH 2 @ TIP | 0.0050 | 0.0008 | 0.0008 |
| LAND WIDTH 1 @ EXIT | 0.0088 | 0.0008 | 0.0008 |
| LAND WIDTH 2 @ EXIT | 0.0108 | 0.0008 | 0.0008 |
| MARGIN WIDTH 1 @ TIP | 0.0020 | 0.0008 | 0.0008 |
| MARGIN WIDTH 2 @ TIP | 0.0019 | 0.0008 | 0.0008 |
| MARGIN WIDTH 1 @ EXIT | 0.0056 | 0.0008 | 0.0008 |
| MARGIN WIDTH 2 @ EXIT | 0.0057 | 0.0008 | 0.0008 |
| WEB THICKNESS @ .02 FROM TIP | 0.0048 | 0.0002 | 0.0002 |
| WEB TAPER RATE (TIP TO .02) | 0.149 | 0.002 | 0.002 |
| WEB TAPER RATE (.02 TO EXIT) | 0.019 | 0.002 | 0.002 |
| POINT ANGLE ($\beta$) | 60° | 2° | 2° |
| PRIMARY ANGLE ($\gamma$) | 15° | 2° | 2° |
| CLOCKING ANGLE ($\alpha$) | 170° | 2° | 2° |
| OVERALL LENGTH | 1.500 | 0.003 | 0.003 |
| REFERENCE DIMENSIONS ONLY | | | |
| RAKE ANGLE @ TIP | −16° | 2° | 2° |
| RAKE ANGLE @ EXIT | $\geq$−15° | | |

This invention has been disclosed and described in the context of various preferred embodiments. It will be understood by those skilled in the art that the present invention extends beyond the specific disclosed embodiments to other alternative possible embodiments, as will be readily apparent to those skilled in the art. Thus, it is intended that the scope of the present invention herein disclosed should not be limited by the disclosure herein, except as encompassed by a fair reading of the claims which follow.

What is claimed is:

1. An endodontic dental instrument for extirpating and enlarging a root canal, comprising a working portion having a length of from about 3 to about 18 millimeters, a diameter ranging from about 0.08 millimeters to about 1.9 millimeters and a web which is tapered and terminates at a tip, and wherein the rate of web taper in a region of said working portion adjacent said tip is greater than the rate of web taper in the remainder of said working portion, at least one helical flute, at least one tissue-removing edge, and at least one outer helical land, the helical flute and helical land each having a pitch ranging from about 1 spiral per 16 millimeters to about 1 spiral per millimeter, at least a portion of said working portion being tapered and terminating at said tip, the rate of taper adjacent said tip being greater than the rate of taper in the remainder of said working portion, wherein the rate of web taper adjacent said tip is between about 0.1 mm/mm and 0.25 mm/mm and wherein the rate of web taper in the remainder of said working portion is between about 0.01 mm/mm and 0.08 mm/mm.

2. The instrument of claim 1 wherein the rate of diameter taper of said working portion adjacent said tip is between about 0.1 mm/mm and 0.25 mm/mm and wherein the rate of diameter taper in the remainder of said working portion is between about 0.01 mm/mm and 0.08 mm/mm.

3. The instrument of claim 1 wherein said tip comprises a chisel tip comprising plural facets which intersect along a substantially linear chisel edge that is substantially orthogonal to a longitudinal axis of the elongate working portion.

4. The instrument of claim 3 wherein said chisel tip has a point angle of approximately sixty degrees.

5. An endodontic dental instrument for extirpating and enlarging a root canal, comprising a working portion having a length of from about 3 to about 18 millimeters, a diameter ranging from about 0.08 millimeters to about 1.9 millimeters, at least one helical flute, at least one tissue-removing edge, and at least one outer helical land, the helical flute and helical land each having a pitch ranging from about 1 spiral per 16 millimeters to about 1 spiral per millimeter, said working portion having a proximal end portion and a distal end portion and terminating at a tip, said distal end portion further including a region of locally enhanced compliance adjacent said tip, wherein said region of enhanced compliance is formed by annealing, heat treating or chemically treating said region to increase the compliance characteristics thereof, whereby said instrument more readily follows the central axis of a curved root canal with less tendency to transport through the canal wall.

6. The instrument of claim 5, wherein said tip comprises a chisel tip comprising plural facets which intersect along a substantially linear chisel edge that is substantially orthogonal to a longitudinal axis of the elongate working portion.

7. The instrument of claim 6 wherein said chisel tip has a point angle of approximately sixty degrees.

8. An endodontic file or reamer instrument for extirpating a root canal, comprising a working portion having a length of from about 3 to about 18 millimeters, a diameter ranging from about 0.08 millimeters to about 1.9 millimeters, at least one helical flute, at least one tissue-removing edge, and at least one outer helical land, the helical flute and helical land each having a pitch ranging from about 1 spiral per 16 millimeters to about 1 spiral per millimeter, said working portion having a proximal end portion and a distal end portion and terminating at a tip, said working portion being divided into at least two regions, including a first region extending from a first point adjacent the proximal end portion to a second point intermediate the proximal and distal end portions and a second region adjacent said first region and extending from said second point to a third point adjacent the distal end portion of said working portion, and wherein said working portion has a stiffness in the first region which decreases substantially continuously along a first curve progressively from said first point to said second point and wherein the stiffness of said working portion in the second region decreases substantially continuously along a second curve, steeper than said first curve, progressively from said second point to said third point.

9. The instrument of claim 8 wherein said working portion has a web which is tapered and terminates at said tip, and wherein the rate of web taper in said second region is greater than the rate of web taper in said first region.

10. The instrument of claim 8 wherein said working portion has an outer diameter which is tapered and terminates at said tip, and wherein the rate of diameter taper in said second region is greater than the rate of diameter taper in said first region.

11. The instrument of claim 8 wherein said second region is formed by annealing, heat treating or chemically treating said region to increase the compliance characteristics thereof.

12. The instrument of claim 8 wherein said tip comprises a chisel tip comprising plural facets which intersect along a substantially linear chisel edge that is substantially orthogonal to a longitudinal axis of the elongate working portion.

13. The instrument of claim 12 wherein said chisel tip has a point angle of about sixty degrees.

* * * * *

UNITED STATES PATENT AND TRADEMARK OFFICE
CERTIFICATE OF CORRECTION

PATENT NO.   : 5,882,198
DATED        : March 16, 1999
INVENTOR(S)  : Tim L. Taylor and John T. McSpadden It is certified that error appears in the above-identified patent and that said Letters Patent is hereby corrected as shown below:

On the title page, after "[22] Filed: June 30, 1997 insert the following:

--Related U.S. Application Data

[60]   Provisional Application Serial No. 60/041,740, March 28, 1997--.

In column 1, line 3, insert the following paragraph:

--This application claims the priority of U.S. Provisional Application Serial No. 60/041,740, filed March 28, 1997 (now abandoned).--

Signed and Sealed this

Tenth Day of August, 1999

*Attest:*

Q. TODD DICKINSON

*Attesting Officer*     *Acting Commissioner of Patents and Trademarks*